US012577559B2

(12) United States Patent
Wu et al.

(10) Patent No.: US 12,577,559 B2
(45) Date of Patent: Mar. 17, 2026

(54) METHOD FOR CREATING A cDNA SEQUENCING LIBRARY

(71) Applicants: Di Wu, Solna (SE); Tomasz Wirt, Enskede (SE); Mats Nilsson Bernitz, Drottningholm (SE)

(72) Inventors: Di Wu, Solna (SE); Tomasz Wirt, Enskede (SE); Mats Nilsson Bernitz, Drottningholm (SE)

(73) Assignees: Di Wu, Solna (SE); Tomasz Wirt, Enskede (SE); Mats Nilsson Bernitz, Drottningholm (SE)

( * ) Notice: Subject to any disclaimer, the term of this patent is extended or adjusted under 35 U.S.C. 154(b) by 1083 days.

(21) Appl. No.: 17/615,311

(22) PCT Filed: Jun. 3, 2020

(86) PCT No.: PCT/EP2020/065292
§ 371 (c)(1),
(2) Date: Nov. 30, 2021

(87) PCT Pub. No.: WO2020/245157
PCT Pub. Date: Dec. 10, 2020

(65) Prior Publication Data
US 2022/0220471 A1      Jul. 14, 2022

(30) Foreign Application Priority Data
Jun. 3, 2019    (SE) .................................... 1950648-4

(51) Int. Cl.
C12N 15/10          (2006.01)
C12Q 1/68          (2018.01)
(Continued)

(52) U.S. Cl.
CPC ....... C12N 15/1096 (2013.01); C12Q 1/6806 (2013.01); C12Q 1/6855 (2013.01);
(Continued)

(58) Field of Classification Search
None
See application file for complete search history.

(56) References Cited

U.S. PATENT DOCUMENTS

| 2014/0120534 A1 | 5/2014 | Bernitz et al. |
| 2016/0138086 A1 | 5/2016 | Seelig et al. |

FOREIGN PATENT DOCUMENTS

| CN | 108103055 A | 6/2018 |
| CN | 109661474 A | 4/2019 |

(Continued)

OTHER PUBLICATIONS (1) Karrer et al., In situ isolation of mRNA from individual plant cells: creation of cell-specific cDNA libraries (Proc. Natl. Acad. Sci.; 1995) (Year: 1995).*

(Continued)

*Primary Examiner* — Heather Calamita
*Assistant Examiner* — Elizabeth Rose Lafave
(74) *Attorney, Agent, or Firm* — MARSHALL, GERSTEIN & BORUN LLP

(57)          ABSTRACT

The present invention relates to the field of biotechnology and a method for creating a cDNA library. More specifically, the invention refers to a method of forming complementary DNA (cDNA) sequencing libraries from RNA in situ comprising the steps of: (a) fixating cells, immobilized on a solid surface; (b) performing an in situ reverse transcription (RT) inside cells, using RT primers comprising a PCR handle 1, and partially biotinylated dNTPs; (c) releasing single stranded cDNA from the cells using a release mix, wherein the release mix comprises an RNAse, such that the single stranded cDNA is released from intact cells; (d) collecting a supernatant comprising released cDNA into a single larger (Continued)

volume or in separate volumes; and (e) introducing an adapter molecule comprising a PCR handle 2 that will bind 3' of the extended cDNA.

18 Claims, 16 Drawing Sheets

(51) Int. Cl.
    *C12Q 1/6806*        (2018.01)
    *C12Q 1/6855*        (2018.01)

(52) U.S. Cl.
    CPC . *C12Q 2525/191* (2013.01); *C12Q 2535/122* (2013.01); *C12Q 2563/179* (2013.01)

(56) References Cited

FOREIGN PATENT DOCUMENTS

| | | | |
|---|---|---|---|
| WO | WO-2015058052 A1 | 4/2015 | |
| WO | WO-2017/040306 A1 | 3/2017 | |
| WO | WO-2017044893 A1 | 3/2017 | |
| WO | WO-2017205686 A1 * | 11/2017 | ............ C12N 15/10 |
| WO | WO-2018013723 A1 | 1/2018 | |
| WO | WO-2019084046 A1 | 5/2019 | |

OTHER PUBLICATIONS (2) Barre et al.; Semiquantitative reverse transcription-polymerase chain reaction analysis of syndecan-1 and -4 messages in cartilage and cultured chondrocytes from osteoarthritic joints (Osteoarthritis and Cartilage; 2000) (Year: 2000).*

(3) Holzmann et al., RNase P without RNA: Identification and Functional Reconstitution of the Human Mitochondrial tRNA Processing Enzyme (Cell; 2008) (Year: 2008).*

(4) Rutsaert et al., In-depth validation of total HIV-1 DNA assays for quantification of various HIV-1 subtypes (Nature; 2018) (Year: 2018).*

Bush et al., PLATE-Seq for genome-wide regulatory network analysis of high-throughput screens, Nat. Commun. 8(105):1-7 (2017).

Ye et al., DRUG-seq for miniaturized high-throughput transcriptome profiling in drug discovery, Nat. Commun. 9(4307):1-9 (2018).

Swedish Patent Application No. 1950648-4, Office Action, dated Nov. 27, 2019.

International Application No. PCT/EP2020/065292, International Search Report and Written Opinion, mailed Aug. 3, 2020.

Krzywkowski et al., Padlock probes to detect single nucleotide polymorphisms, Methods Mol. Biol., 1649:209-229 (2018).

Krzywkowski, iLocks: a novel tool for RNA assays with improved specificity, Doctoral Thesis, Department of Biochemistry and Biophysics, Stockholm University, 62 pp. (2017).

Lee et al., Highly multiplexed subcellular RNA sequencing in situ, Science, 343(6177):1360-3 (Mar. 2014).

Bray et al., Cell Painting, a high-content image-based assay for morphological profiling using multiplexed fluorescent dyes, Nat. Protoc., 11(9):1757-74 (2016).

Chomczynski et al., Single-step method of RNA isolation by acid guanidinium thiocyanate-phenol-chloroform extraction, Anal. Biochem., 162(1):156-9 (1987).

Lao et al., mRNA-sequencing whole transcriptome analysis of a single cell on the solidTM system, J. Biomol. Tech., 20(5):266-71 (2009).

Ramskold et al., Full-length mRNA-Seq from single-cell levels of RNA and individual circulating tumor cells, Nat. Biotechnol., 30(8):777-82 (2012).

Sakaue-Sawano et al., Visualizing spatiotemporal dynamics of multicellular cell-cycle progression, Cell, 132(3):487-98 (2008).

Gustafsdottir et al., Multiplex cytological profiling assay to measure diverse cellular states, PLoS One, 8(12):e80999 (2013).

Subramanian et al., A Next Generation Connectivity Map: L1000 Platform and the First 1,000,000 Profiles, Cell, 171(6):143752.e& (2017).

* cited by examiner

101: RNA insitu
102: cDNA primer with W.ID and PCR handle 1 and 3
103: extened cDNA primer
104: Adapter with P.ID.S and PCR handle 2 and 4
105: Full-length libary product for sequencing

Figure 4

101: RNA insitu
102: cDNA primer with W.ID and PCR handle 1 and 3
103: extened cDNA primer
104: Adapter with P.ID.S and PCR handle 2 and 4
105: Full-length libary product for sequencing Lane   1   2   3   4   5   6   7   8   9   10   11   12   13   14

Before purification       After purification

No biotinylated
dNTPs

Biotinylated
dCTPs

Biotinylated
dUTPs

ACTB

MALAT
TALAM1  MASCRNA

☐ mRNA

Other RNA

■ lncRNA 0,03% rRNA 0,04% miRNA 1,37%

3,14%

95,42%

A

B

ACTB gene

SKBR3

SKOV3

BJhTERT

Breast Cancer
Fresh Frozen

Breast Cancer
Fresh Frozen,
no beads

Breast Cancer
FFPE

Prostate Cancer
Fresh Frozen

ACTB

METHOD FOR CREATING A cDNA SEQUENCING LIBRARY

CROSS-REFERENCE TO RELATED APPLICATIONS

This application is a U.S. national phase of International Patent Application No. PCT/EP2020/065292, filed on 3 Jun. 2020, which claims priority benefit under § 119 to Sweden Patent Application No. 1950648-4, filed on 3 Jun. 2019.

TECHNICAL FIELD

The present invention relates to the field of biotechnology and a method for creating a cDNA library.

BACKGROUND ART

Genes encoded in DNA are copied to messenger RNA molecules (mRNA) before they can be translated into effector proteins. Abundance and type of mRNA, or gene expression, can be used as a biomarker that reveals a drug's mechanisms of action, or deliver valuable information of a cell's state at any given time point. During the last decade, chemistry and specialized platforms were developed that are able to decode or sequence a cell's RNA content. RNA sequencing (RNA-seq) as a technique for RNA analysis became a popular technique and is widely adapted.

Prior to sequencing, RNA content has to be extracted from cells and isolated, and transformed into a library preparation to ensure compatibility with sequencing instruments. While RNA-seq procedures are easily scalable and automatable, isolation of RNA used in sequencing library preparation is normally based on an organic solvent and solid phase extraction procedures. In the RNA-seq of prior art, a cumbersome and low-throughput RNA isolation step is limiting for the method to be a low cost and high-throughput gene expression readout technique.

Next generation sequencing (NGS) become a technology workhorse revealing deep insights into complexity of life as well as a disease. Identification of somatic mutations reveals risk loci for heritable diseases or mechanisms underlying various cancers. Expression of genes is timely regulated, and it reflects cellular fitness and response in the given environment conditions. RNA sequencing—being in the spotlight during last years—allows us to understand why, when and what kind of genes are expressed that eventually lead to a cellular response, a phenotype. Phenotypic information (shape and size of organisms, cells as well as subcellular components) has been, and still is in many occasions, giving basis for understanding how cells react. To understand the property of the effect in depth, researches perform parallel model cells perturbations and phenotypically measure the consequences (cellular toxicity, migration, subcellular transport of components). Such compounds screens play crucial role in the discovery of novel therapeutics, their inhibitors as well as exact targets. Majority of pharmaceutical screens rely on phenotype analysis of cells, mostly because technologies allowing for systematic approach into gene expression are not easily available or implementable. A challenge is to understand connections between perturbants mechanisms of action (MoA), expressed responses and phenotypical effect.

Due to the limitations listed above, high throughput drug screening (HTS) is limited to cost-effective reporters or phenotypic information alone. For example, polyploidization of cells or intensified ER/Golgi staining suggest a chemical as a tubulin modulator or neuronal modulator respectively (States et al., 2013). A key advantage of transcriptome-wise reporters is convenience of perturbating cells without limiting the number or type of measured features. To date, RNA sequencing procedures have been optimized and are readily available for hundreds of samples to be run in parallel. Currently, the majority of RNA sequencing-based experiments input material is still harvested using traditional trizol-based extraction procedures (Chomczynski & Sacchi, 1987). In last years, new methods have emerged where cells are grown in multi-well plates, lysed and RNA content prepared prior sequencing. In L1000 platform, expression of 1000 genes is measured and remaining genes are inputted in silico (Subramanian et al., 2017). This approach laid foundation for the Connectivity Map (CMAP) platform, storing a collection of phenotypic data of various perturbants, including chemicals and shRNAs. In PLATE-seq method, cells grown in 96 oligo(dT) grafted well plates were lysed and RNA processed in parallel with a final gene expression profiling cost for approximately 15$ per sample (Bush et al., 2017). Laborious RNA purification steps and relatively small scale limit the number of parameters that can be measured simultaneously. Recently, DRUG-seq method proposed a cheaper alternative (4$ per sample) and was used in transcriptome-wide compounds MoA screen in 384-well format (Ye et al., 2018). This method currently presents a most affordable solution suitable for HTS screening environment. Both methods above, PLATE- and DRUG-seq, propose own systems of cDNA labelling to maximize the multiplexing and sequencing capacity. Also, authors of both methods utilize 3'-end polyA (A) tailing of cDNAs sacrificing whole mRNA sequencing coverage. Such approach poses risk of introduction of unintentional 3'-end bias and hampers detection of significant differences in alternatively spliced genes (Lao et al., 2009; Ramsköld et al., 2012). Finally, RNA in L1000, PLATE- and DRUG-seq methods is obtained from the cell lysate after HTS experiment and biological sample is permanently lost.

Further, US2016138086 discloses a method for labelling and barcoding molecules such as RNA and cDNA within a cell, using e.g. reverse transcription.

SUMMARY OF THE INVENTION

The object of the present invention is to provide a method for generating RNA sequencing libraries at high-throughput and a low cost. The object of the present invention is further to provide a method that is scalable and can be used for both single samples up to thousands of samples. It is a further object to provide a method that is rapid and conveniently performed.

The inventors have identified a method for generating RNA sequencing libraries that combines very basic and robust molecular reactions in a new format. The method of the present invention allows rapid and scalable generation of sequencing libraries derived from cellular RNA, omitting RNA isolation or ribosomal RNA depletion. The present method can be performed in a simple and high throughput manner at a low cost. Thus, the method of the present invention provides for a full and unbiassed RNA coverage, transcriptome-wide RNA sequencing approach, bypassing RNA isolation. In this approach, cDNA synthesis is not performed on RNAs present in the cell lysate, but on RNA directly in situ. The method of the present invention is named RNA Isolation Free Sequencing, RIF-Seq.

Thus, the objects above are attained in a first aspect by a method of forming complementary DNA (cDNA) sequencing libraries from RNA in situ comprising the steps of a) fixating cells, immobilized on a solid surface;

b) performing an in situ reverse transcription (RT) inside cells, using RT primers comprising a PCR handle 1, and partially biotinylated dNTPs;

c) releasing single stranded cDNA from the cells using a release mix, wherein the release mix comprises an RNAse, such that the single stranded cDNA is released from intact, unlysed, cells;

d) collecting a supernatant comprising released cDNA into a single larger volume or in separate volumes;

e) introducing an adapter molecule comprising a PCR handle 2 that will bind 3' of the extended cDNA.

In the context of this invention, the term "cells" include any cells, cellular material or cell-like particles that contains genetic information in a cell-like environment. Thus, "cells" can be chosen from eukaryotic cells of human or non-human origin, prokaryotic cells of bacteria or archaea domain, or cell-like particles, such as viral particles.

According to some embodiments, the immobilization of cells to the solid surface occurs spontaneously, as an effect of an inherent feature of the cells. For example, this can be achieved by adherent epithelial cells that readily attach to a variety of surfaces or biofilm-forming bacteria.

According to some embodiments, the immobilization of cells to the solid surface occurs by gravity or pressure induced forces, for cells that are present in liquid suspension.

According to some embodiments, the immobilization of cells to the solid surface occurs artificially using chemical or biological reagents that increases the affinity of the cell to the surface.

According to some embodiments, the RT primer in step b) further comprises a well specific barcode sequence (W.ID), and a concentration of the released cDNA is performed as a step d2) after step d) and before step e).

According to some embodiments, a concentration of the PCR handle-containing cDNA is performed as a step e2) after step e).

According to one embodiment, the method further comprises the step of f) a first amplification of the PCR handle-containing cDNAs from step e) in order to obtain a first product mix.

According to a further embodiment, the method further comprises the steps of g) a PCR extension step using indexing primers comprising a PCR handle 3 or a PCR handle 4, complementary to the 5' PCR handle 1 and 3' PCR handle 2, respectively, in order to obtain a second product mix (h) a second PCR amplification of the second product mix obtained in step g) using PCR primers complementary to the PCR handles 3 and 4 in order to obtain a third product mix.

According to a further embodiment, indexing primers are used in step g) comprising plate indicating sequences (P.ID.S), said P.ID.S being a first P.ID.S. on the 3' primer and a second P.ID.S on the 5' primer.

According to another further embodiment, the PCR extension step in step g) is performed with a P.ID.S on either of the 3' or 5' primer and/or well specific barcode sequence (W.ID) on either of the 3' or 5' primer.

According to yet a further embodiment, the separate volumes of the third product mix may be pooled prior to a sequencing.

According to another embodiment, the RT primer in step b) further comprises either a plate indicating sequences (P.ID.S) or well specific barcode sequence (W.ID) and a PCR handle 3, and the adapter molecule in step e) further comprises either a plate indicating sequences (P.ID.S) or a well specific barcode sequence (W.ID) and a PCR handle 4, under the provision that the RT primer and the adapter molecule do not contain the same identification sequence, i.e. when the RT primer comprises a P.ID.S, the adapter molecule comprises a W.ID., and when the RT primer comprises a W.ID, the adapter molecule comprises a P.ID.S.

According to yet another embodiment, the method further comprises an imaging step of the remaining unlysed cells after step d).

DESCRIPTION OF THE DRAWINGS

FIG. 4. RT primer and sequencing library components. A) 1st embodiment RT primers (top) consist P1: 1st PCR handle 1 (sequencing primer/adapter sequence, later used in 1st PCR reaction); W.ID: a unique, area specific 8-nucleotide long barcode; [N]10: randomized 10 nucleotides that serve as both priming sequence and also as a unique molecular identifier (UMI). During second step, adapter is ligated. During indexing step, Plate-specific (P.ID.S) sequences are added to the libraries on either or both 3' and 5' end. After the RIF-Seq protocol is applied, sequencing libraries are composed of cDNA: W.ID: well specific barcode; P1/2: flanking PCR handle sequences utilized in the 1st PCR reaction as well as plate indexing; P.ID.S1/2: plate indexes sequences, used in parallel HTS screen and to maximize sequencing capacity; P3/4: flanking 2nd PCR handle sequences utilized in 2st PCR reaction and sequencing. B) 2nd embodiment RT primers contain 1st PCR P1 handle and random 10 nucleotides. During second step adapter is ligated. During indexing step, plate- or/and well-specific sequences can be added on either 375' end (marked with asterisk *). After the RIF-Seq protocol is applied, sequencing libraries are composed of cDNA, P1/2: flanking 1st PCR handle sequences utilized in the 1st PCR reaction as well as plate indexing; W.ID+P.ID.S: well and plate indexes sequences, used in parallel HTS screen and to maximize sequencing capacity; P3/4: flanking 2nd PCR handle sequences utilized in 2st PCR reaction and sequencing. C) In the last approach, to reduce number of indexing steps, W.ID, P.ID.S, and 2nd PCR handles can be added directly to RT primer and 3' adapter sequences. W.ID and P.ID.S can be put in either RT primer or adapter sequence (marked with asterisk *). Black triangles represent 3' termini of DNA FIG. 5. A: According to example 2 (where no well specific barcodes were present in RT primers) the adapter ligated cDNA (lane 3-5) was amplified in second PCR amplification step. The PCR products were analyzed by agarose gel electrophoresis stained with sybr green to visualize the DNA bands. The DNA ladder (lane 1 and 6) were included to indicate the length of bands. The ligation dimmer (lane2), in which no dNTP was added during the cDNA synthesis step was used as control. Lanes 3-5 contain properly amplified cDNA libraries, seen as a characteristic DNA smear of varied length 100-350 base pairs. B,C,D: Bioanalyzer DNA1000 analysis of the cDNAs extended and amplified on various steps of the pipeline according to example 1 (where well specific barcodes were present in RT primers). B: Products of the first amplification of the PCR handle-containing cDNAs from step-first product mix. Average product size is ~120 bp. C: Products of a a PCR extension step-second product mix. Average product size is ~210 bp. D: a second PCR amplification of the second product mix-third product mix, final cDNA library.

B: Upper panel: RIF-Seq using a set of 384 barcodes (barcodes were placed on the 384 plate individually) on 3 different cell lines in a 384-well plate (each cell line was present in in 128 wells) according to the plate schematic. Lower panel: histogram presenting overall distributions of number of genes detect in each cell line group, including their median values.

Figure 12:
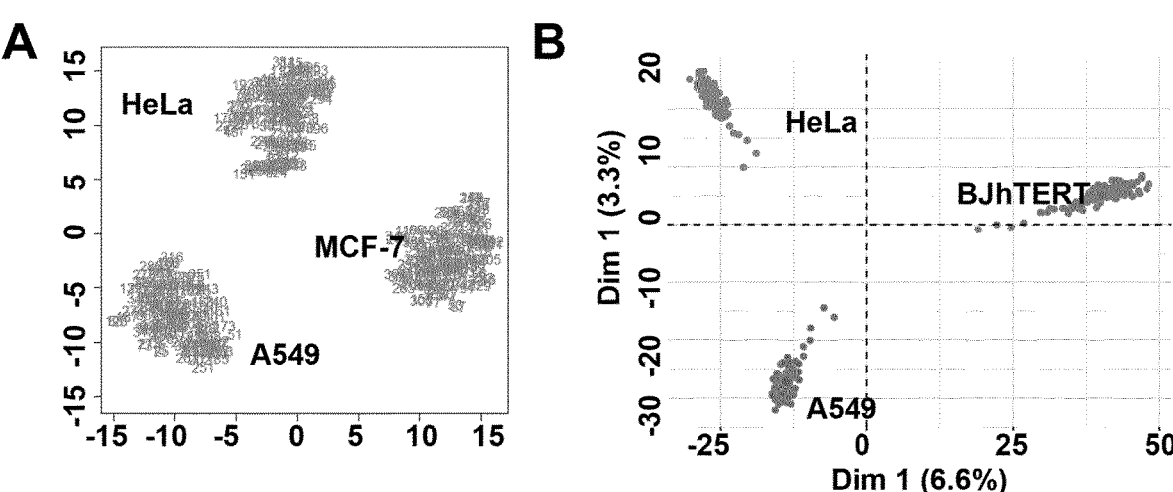

FIG. 12. A: RIF-Seq using a set of 384 barcodes (4 barcodes per well) on 3 different cell lines in a 96-well plate (each cell line was present in in 32 wells). Samples clustered by t-sne using the gene expression values. B: RIF-Seq using a set of 384 barcodes on 3 different cell lines in a 384-well plate (each cell line was present in in 128 wells). Samples clustered by PCA using the gene expression values FIG. 13. A: Cartoon depicting RIF-Seq protocol applied on mouse brain tissue section. Four droplets with RT reaction mix were additionally supplied with DNA staining reagent (DAPI). B: cDNAs were mapped to the reference RNA database presenting that RIF-Seq can be applied on mouse brain tissue to deliver spatial information from the tissue.

Figure 14:
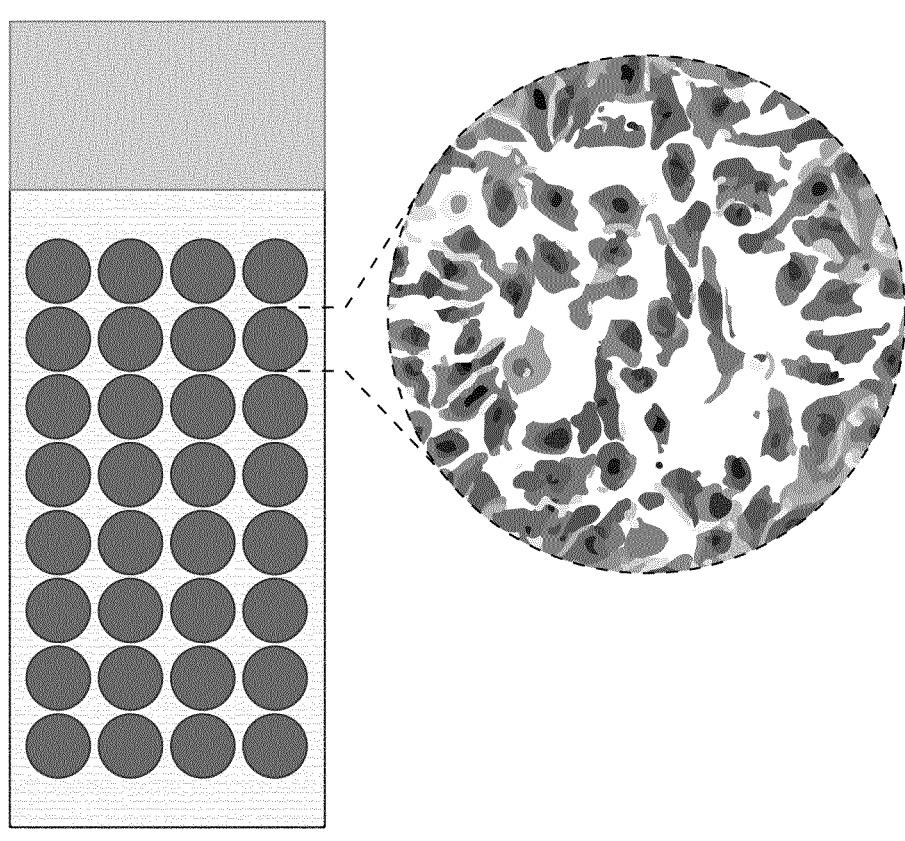

FIG. 14. Cartoon depicting RIF-Seq protocol applied on cells cultured on a microscope slide. RT mix containing DNA staining agent (DAPI) was added as 32 individual droplets.

Figure 15:
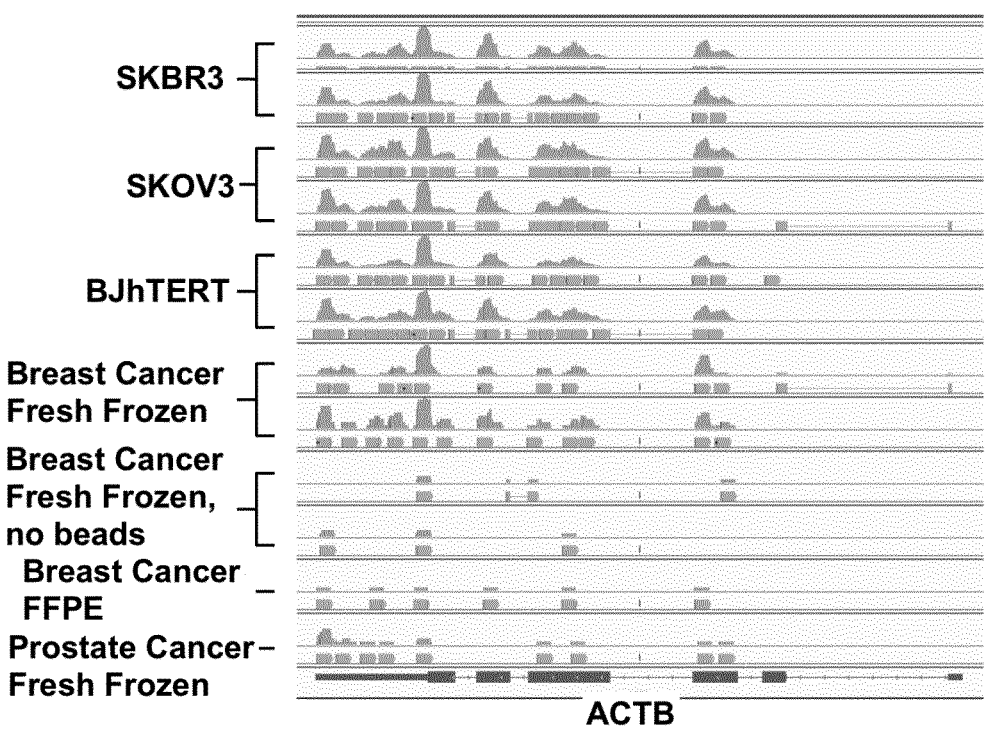

FIG. 15. cDNA mapping to the reference genome for various samples. For simplicity, only cDNAs mapped to ACTB gene are presented. The height of peaks indicate the abundance of mapped reads for different sample (separated by different tracks). Top 3 mapping charts are shown for other cell lines (SKBR3, SKOV3 and BjhTERT). Below, Rif-seq was applied on various type of tissue sections (frozen breast; frozen breast where magnetic beads purification step was not performed; breast cancer paraffin embedded; prostate cancer paraffin imbedded).

Figure 16:
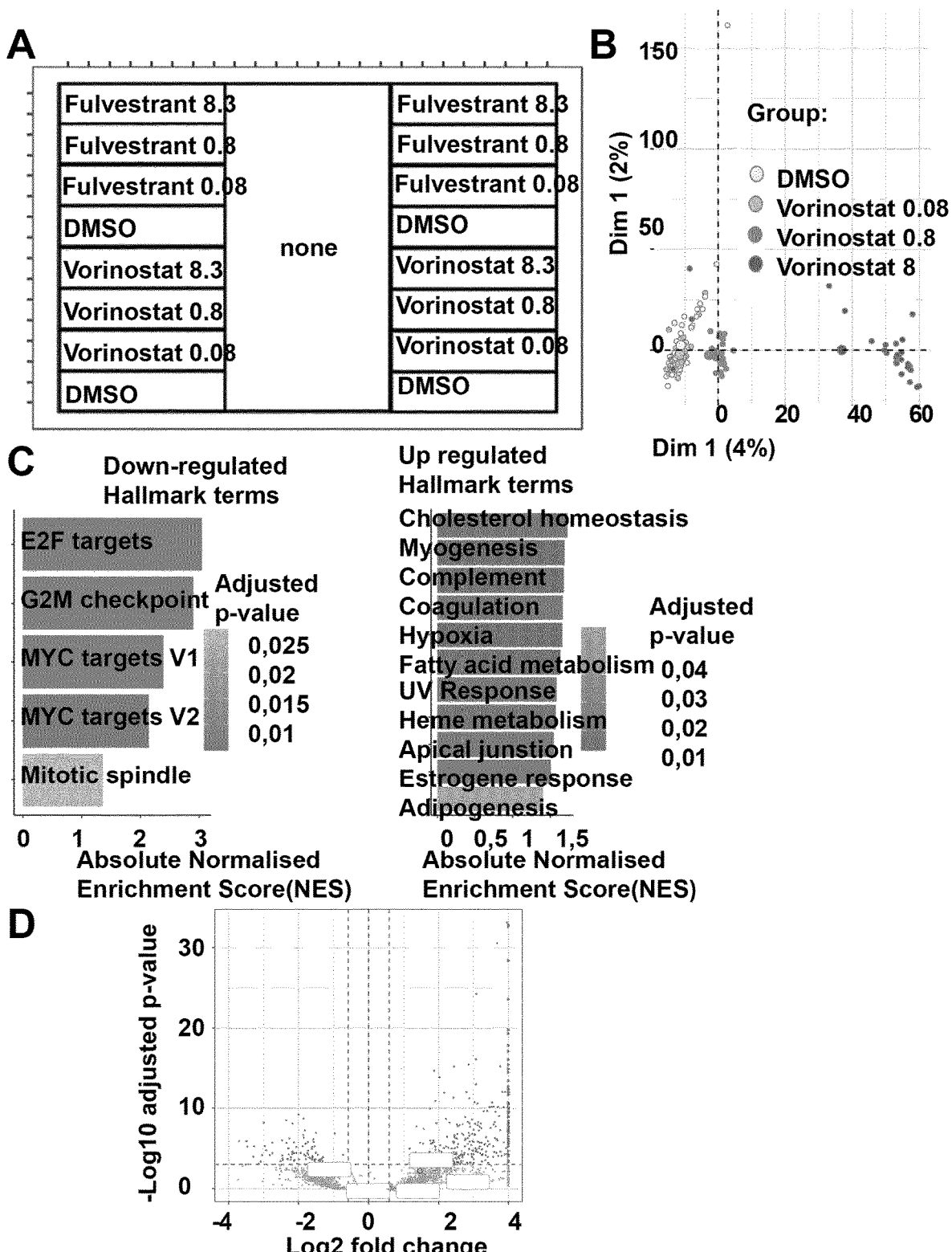

FIG. 16. A: Plate schematic of RIF-Seq screen of two compounds in various concentration and DMSO controls. All concentrations are in µM. B: PCA analyses of DMSO controls and samples that were treated with vorinostat at different concentrations. C: Gene Set Enrichment Analysis (GESA) of samples treated with 8.3 µM vorinostat and controls. D: Volcano plot of genes over- and under-expressed upon treatment with vorinostat at 8.3 µM concentration.

DETAILED DESCRIPTION

The invention will now be described in more detail. However, it is to be understood that the embodiments and examples as disclosed herein are exemplary, and is not intended to limit the scope of the present disclosure.

As disclosed above, the present invention relates to a method for preparing a cDNA sequencing library. Thus, it relates to a method of forming complementary DNA (cDNA) sequencing libraries from RNA in situ comprising the steps of a) fixating cells, immobilized on a solid surface;
   b) performing an in situ reverse transcription (RT) inside cells, using RT primers comprising a PCR handle 1, and partially biotinylated dNTPs;
   c) releasing single stranded cDNA from the cells using a release mix, wherein the release mix comprises an RNAse, such that the single stranded cDNA is released from intact, unlysed, cells;
   d) collecting a supernatant comprising released cDNA into a single larger volume or in separate volumes;
   e) introducing an adapter molecule comprising a PCR handle 2 that will bind 3' of the extended cDNA.

The cells are chosen from eukaryotic cells of human or non-human origin, prokaryotic cells of bacteria or archaea domain. The cells may also be chosen from other cellular material or cell-like particles, such as viral particles, including genetic code that can be used in the methods of the invention.

The solid surface may be in the form of a slide, a petri dish, or a multi-well plate, such as a 4-well, 6-well, 12-well, 24-well, 48-well, 96-well, 384-well or a 1536-well plate. The choice of number of wells is dependent on the number of analyses and samples required for an experiment, and the skilled person will be readily able to determine which type of solid support is the most suitable one for the experiment to be performed. The larger number of wells a plate has, the higher throughput will be possible using the method of the present disclosure.

The immobilization of cells or cell-like particles to the solid surface may occur in various ways. For example, cells that are adherent cells, grow spontaneously directly on a surface, e.g. chamber slides, bottom of 6/12/24/96/384/1536-well plate, glass slides. HeLa, A549, HEK 293, epithelial primary cells are examples of eukaryotic cells readily adhering to surfaces. Further, bacteria from genera *Bacteroides, Clostridium, Faecalibacterium, Eubacterium, Ruminococcus, Peptococcus, Peptostreptococcus, Bifidobacterium, Escherichia* and *Lactobacillus* readily form biofilms on solid surfaces. The cells are in a tissue section, harvested from animal or biopsy material, can be passively attached to a glass slide. By using cylindrical tissue cores, different part of a tissue can be placed on the same glass slide as tissue microarray. The cells, non-adherent by nature or growing in suspension, can be immobilized to a surface by centrifugation to a surface or with some special equipment e.g Cytospin™. BJAB, Jurkat, human or non-human primary B cells are examples of eukaryotic cells cultured in suspension. The cells non-adherent by nature or growing in suspension can also be captured to a surface by capturing affinity reagents, e.g. antibodies, which captured certain surface molecular markers on the cell; by pre-coating attachment surface with poly-L/D-lysine. Virus particles can be immobilized to the solid surface by modifying capsid proteins or lipids (functionalization) followed by covalent immobilization to functional surface through click chemistry. Examples of viruses that can be immobilized on the surface are influenza virus from Orthomyxoviridae family, coronavirus from Coronaviridae family. Furthermore, affinity of cells to a surface can be further enhanced by supplementing growth media with extra cellular matrix proteins, fibronectin, elastin, laminin, collagen or other agents/molecules increasing cell adhesion properties. The cells with certain sizes can be captured to a filtering surface with the pore size smaller than the cell, so that cells become immobilized on the pores on the surface.

The cells may be a homogenic or a heterogenic collection of cells. That is, they may be from one or more cell cultures, or may be in the form of a tissue that has been immobilized on the solid surface. It may thus relate to cultured cells, tissue sections, or tissue microarrays, TMAs. The cells may be of human origin, or of non-human origin. The cells may be 3D sphere cultured cells or 3D cell spheroids.

The immobilized cells are subjected to fixing to preserve and cross-link cellular components in place, inside the cells. Fixing and cross-linking limits unwanted diffusion and loss of cellular RNA and is preferably conducted using 3.7%-4% formaldehyde. Other fixatives may include paraformaldehyde, acetic acid, alcohol solvents and the skilled person is well aware of how to perform a fixation reaction. Preferably after cell fixation, permeabilization step is conducted in to create gentle alteration in cell body allowing reagent access to intercellular components such as RNA. Common permeabilizing agents include mild acid treatments (hydrochloric acid) alcohols (ethanol), nonionic surfactants (such as Tween® 20, Triton X-100). On bacterial cells, cellular material or cell-like particles, such as viral particles, custom permeabilization agents may need to be used to provide access through bacterial wall or viral capsid. Those may include enzymes (lysozyme, pepsin, proteinase) or combinations of before mentioned agents. The skilled person is aware of how to perform a permeabilization reaction optimal for cells or cell-like particles.

The Reverse Transcription (RT) that is performed in the immobilized cells is a standard RT reaction. During RT, an enzyme called reverse transcriptase elongates a primer making unique, cDNAs of varying length, hybridized to template RNAs. The skilled person is well aware of how to perform a RT reaction. By performing the RT reaction, the mRNA, or transcripts, in the cell are transformed to complementary DNA, cDNA. During RT, folded and/or double stranded RNAs, for example ribosomal RNA and some parts of mRNA, will be natively "secured" from priming for a RT reaction, and will be subject to the transcription process to a lesser extent. Thus, about as much as 95% of sequencing reads performed in the reaction are mapping to mRNA, and RNA exclusion is thus not required for the presented invention.

Thus, with the present method the RT is performed within the cells, without any previous isolation of mRNA from the cells. This is an important aspect of the present method as an otherwise time-consuming step is eliminated from the method. This also means that the cells may be kept intact or unlysed during the RT, as there is no need to lyse the cells in order to isolate the mRNA. This is particularly important for certain embodiments of the present invention, where it is desirable to keep the cells unlysed for further analysis.

The RT primers used in the present method comprise a pool of random sequences, positioned at the 3' end of the primer. The random sequences are between 5-20 bases, preferably 10 bases long random sequences, and are hereinafter are referred to as 3' decamers. The use of 3' decamers in the RT primers (e.g. a random decamer with a 5' overhang) ensures an unbiased and global RT of the transcripts present in the cell. Further, the RT primer may be configured to reverse transcribe RNA having a poly(A) tail (e.g. a poly(dT) primer, such as a dT(15) primer, with a 5' overhang). Moreover, the RT primer may be configured to reverse transcribe predetermined RNAs (e.g. a transcript-specific primer). For example, the RT primer may be configured to barcode specific transcripts such that fewer transcripts may be profiled per cell, but such that each of the transcripts may be profiled over a greater number of cells.

For RT of cells or tissue immobilized on a solid surface without separate wells, such as a slide, the person carrying out the experiment will determine if and how the cells or tissue should be "compartmentalized" in applying a predetermined primer pattern. By applying a primers in a predetermined pattern, it is possible to separate the results, or sequencing data, from individual locations on the tissue slide or tissue section.

For example, droplets of a RT mix with barcoded cDNA primers can be spotted separately on defined preferably small regions on a tissue slide. To avoid evaporation of RT mix during the reaction, microfluidic chamber or oil can be applied on top of the tissue to protect the droplet from evaporation. The RT primers further comprise a PCR Handle 1, which is conserved in all primers used. The PCR handle 1 is about 25-35 bases long, and may be chosen depending on the sequencing platform that will be used. For instance, the sequences used for the Illumina® sequencing devices may be used, compatible with Illumina® sequencers such as MiSeq™, NextSeq 500™, or NovaSeq™. However, if another sequencing platform is used, the PCR handle should be adapted to that particular platform, and the skilled person is capable of determining the sequences to be used in each particular case.

In the RT reaction, biotinylated dNTPs, dNTPs conjugated with a biotin molecule, are supplied to the reaction for the production of the cDNA.

For the RT reaction, each well will receive the same reaction mixture except for the primers, which may be specific for each well or which may be the same for all wells. The number of RT primers used in a method will correspond to the number of wells on a plate. For example, for a plate of 384 wells, 384 RT primers will be used if 1 primer per well is desired. Thereby, in each well, a whole mRNA transcriptome will be transformed to cDNAs, each cDNA molecule containing the specific RT primer added to that specific well. Even in same exons of two different mRNA molecules, cDNA synthesis will likely begin from different positions. This leads to a randomization that is important for assessing mRNA copy numbers and effective gene expression rate. cDNA randomization will also arise from the fact that during RT, not all ten random bases in the 3' decamer will perfectly match the target mRNA molecule. While terminal 3' bases of the primer have to match perfectly to initiate RT, a 10 bases long complementarity, especially close to the 5' end of the 3' decamer, is not required. It is expected that some random bases in the decamer will also differ between cDNAs. Even if cDNA synthesis will begin from exactly the same place, sequence variability is expected.

The release mix is added to the cells in order to release the cDNA formed during the RT from the intact cells. The cDNA formed in the RT is normally in the form of heteroduplexes with the mRNA within the cell. The release mix will separate the cDNA from the mRNA and allow it to enter the supernatant of the well, or other liquid media surrounding the cell culture when a multi-well plate is not used.

In the present method, the release mix comprises an RNAse, such as RNAseA or RNAseH. RNAseH is a RNA endonuclease that cleaves mRNA in mRNA/cDNA heteroduplexes specifically. When the RNAseH acts on a synthesized cDNA, it will remove the original mRNA molecule, liberating a single stranded cDNA. Thereafter the single stranded cDNA is released from the intact cells into the liquid release mix. The single stranded cDNA will diffuse out of the cells without any further action being necessary. Thus, the cDNA is released without lysing the cells. This is advantageous and important especially for embodiments of the invention where it is desirable to keep the cells unlysed for further analysis.

Once the single stranded cDNA has been released from the cells, the supernatant comprising said single stranded cDNA is collected. The collected supernatants from each well may be kept separate, or they may be pooled to a single larger volume.

At this stage, when using a RNAseH to separate and release the cDNA, in order not to influence any steps downstream, RNaseH may be inactivated. The skilled person is well aware of how to accomplish this inactivation of the enzyme without compromising the samples or subsequent method steps. Inactivation with high temperature, heat, is preferred when RNAseH is used.

After the collection of the supernatants, a double stranded adapter molecule is added to each volume. The adapter molecule comprises a degenerated hexamer overhang, or a 3' randomized part, allowing for ligation with any cDNA present, and further comprises a PCR handle 2, 5' from the overhang. The adapter molecule is preferably introduced to the cDNA by DNA ligation. The adapter molecule will bind juxtaposed to the 3' end of the cDNA with the 3' randomized part on a longer first strand, and ligate the PCR handle 2 to the 3' end of cDNA strand by ligating the 5' terminal end of a second strand of the adapter molecule to the 3' end of the cDNA (See for instance FIG. 2). The 3' randomized part of the first strand serves to anchor the adapter molecule to any cDNA molecule present in the supernatant. The adapter molecule is therefore compatible with any cDNA produced during R.T. in step b). Thus, the cDNA strand is enclosed between a PCR handle 1 on the 5' end and a PCR handle 2 on the 3' end. Furthermore, the adapter molecule is protected at its 3' end, e.g. by amine modification, in order to inhibit ligation between adapters. In this step, a T4 DNA ligase is normally added together with the adapter molecules in order to join the second strand of the adapter molecule to the released cDNA molecule. The skilled person will be able to identify any other enzyme that may be used for the purpose of ligating or binding the second strand to the cDNA. Alternatively, the adapter sequence can also be introduced by DNA polymerization using a primer comprising PCR handle 2' and the above described random priming sequence. Thus, a DNA polymerase may be added to the reaction to be incorporated with and extend the cDNA. Also, in this case, the adapter molecule is protected at the 3' end to prevent unwanted extensions. The polymerase could extend cDNA with the PCR handle 2 sequence, complementary to PCR handle P2'.

According to a first embodiment of the method above, the RT primer in step b) may further comprise a well specific barcode sequence (W.ID). Thus, in this embodiment a separate W.ID is used for each well on a multi-well plate. Thereby it is possible to identify which cDNA originates from which well. Furthermore, this allows for the possibility to pool all the samples of a multi-well plate in step d) of the method. Thus, one pooled sample per plate would be processed further. Such a possibility leads to the ability to perform a more cost-efficient process downstream of step d), as all further steps and/or reactions may be done in larger batches. It is also less time-consuming to handle a single volume than for instance 384 samples, when using a 384-well plate.

In the present method, 10 randomized (degenerated) nucleotides serve both as cDNA priming sequence and also as a unique molecular identifier (UMI). Sequence differences in cDNA and UMI allows for precise differentiation between different cDNAs originated from the same mRNA transcript and duplicated cDNAs introduced from PCR. In other embodiments, a specific UMI sequence can be introduced to RT primers between 3' random decamer and W.ID or 5' from W.ID sequence.

Figure 1:
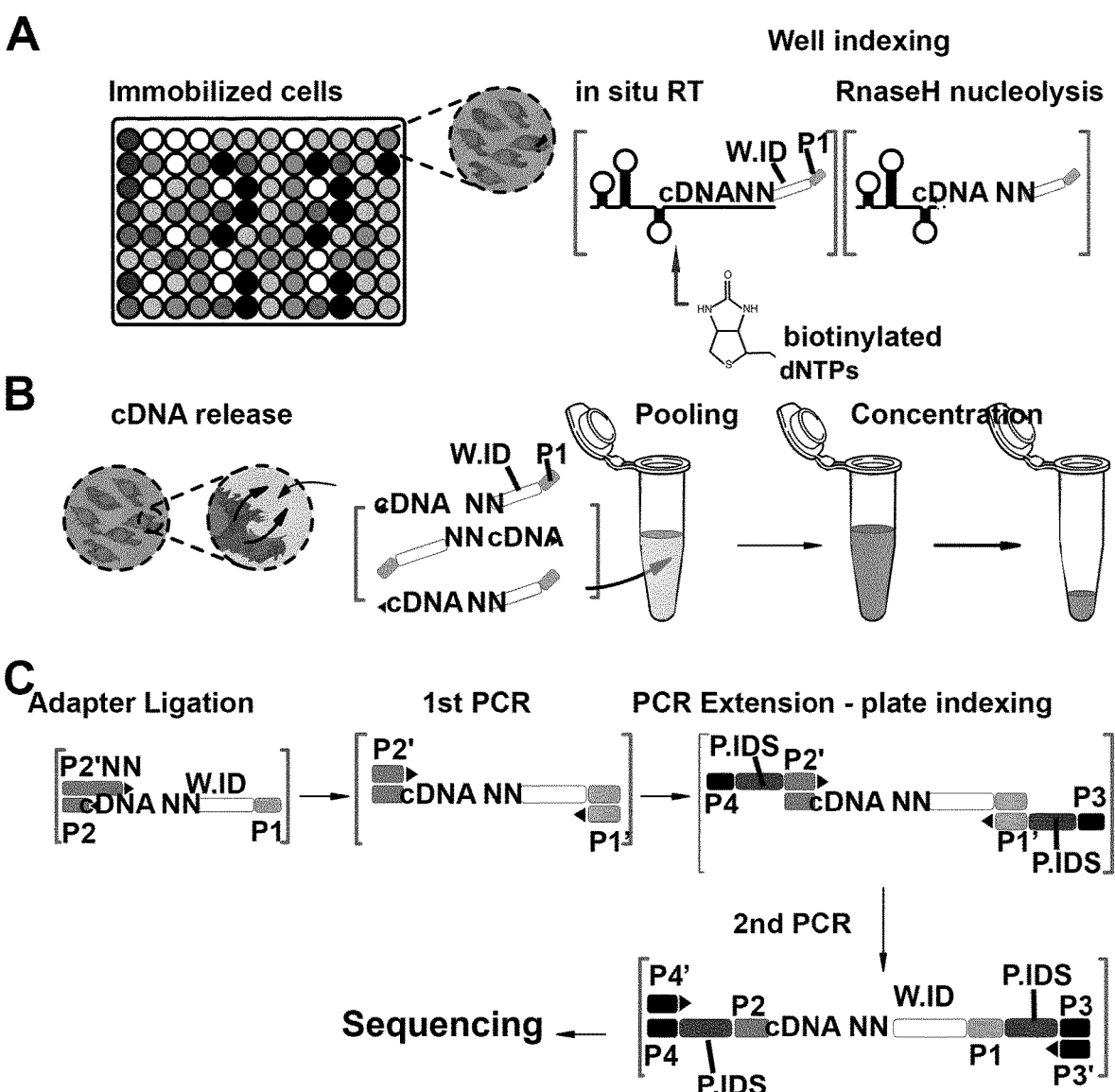
FIG. 1. Example of protocol of RIF-Seq according to a first embodiment. A. Cells used in the experiment are immobilized are fixed. Next, RT master mix containing RT primers, composed of well-unique barcodes (W.ID), PCR handle (P1) and random decamer sequence (NN), and partially biotinylated dNTP are dispensed into each well. After RT, cells are washed and RnaseH is added to degrade RNA. B. cDNAs is passively released into supernatant and supernatants from all wells are pooled in a single volume, one volume per plate. Using biotin incorporated in cDNA sequence, cDNAs are captured on magnetic beads and the reaction volume is concentrated. C. Sequencing libraries are generated. Adapters, composed of shorter fragment with PCR handle 2 (P2) and longer fragment composed of P2-complementary sequence and degenerate 3' (NN) are ligated 3' to the cDNAs leaving a cDNA insert flanked with 1st PCR handles P1 and P2. Unligated adapters are removed by washing magnetic beads. After 1st round of PCR, cDNAs are indexed with unique plate-specific barcodes (P.IDS), one- or two-sided depending on the desired experiment scale. In a second PCR reaction, flanking P3/4 PCR handles are used for final library amplification FIG. 2. Protocol of RIF-Seq, simplified. 101: RNA in situ. 102: cDNA primer with W ID and 1st PCR handle. 103: extended cDNA primer. 104: Adapter with 1$^{st}$ PCR handle 2-105: intermediate library product. 106: PCR primer with P.ID.S1 and PCR handles 2 and 4. 107: PCR primer with P.ID.S2 and PCR handles 1 and 3. 108: Full length library product for sequencing.

With reference to the Figures, FIG. 1 discloses a first embodiment of the present invention. FIG. 1A shows that the cells are adhered to the surface of the plate and fixated after being subjected to different compound treatments. Thereafter well indexing is performed by in situ, whole transcriptome cDNA synthesis using biotinylated dNTPs, followed by in situ RNA nucleolysis from cDNA/RNA duplexes using RNAseH. FIG. 1B illustrates that the cDNA is passively released and flows into the supernatant, leaving cells intact, unlysed. Thereafter supernatants from all wells are pooled in a single volume. Streptavidin coated magnetic beads are added to the sample pool and cDNAs are thus concentrated. FIG. 1C illustrates that in the beads suspension, adapter is ligated 3' to all cDNAs. Thereafter free adapter is removed and the cDNAs are separated from the beads with proteinase and the beads discarded. The cDNA is subjected to a first PCR for cDNA amplification, followed by a plate indexing PCR extension which normally only encompass a few cycles, such as one or two cycles. Thereafter a second PCR is performed which will generate the cDNA library ready to be sequenced. The sequencing of the library does not form part of the scope of the present invention.

The well specific barcode sequence (W.ID) according to any embodiment of the present invention is a barcode sequence of 1-50 nucleotides, preferably 5-30, more preferably 5-20, even more preferably 5-15 and most preferably 8-10 nucleotides. 8 nucleotides is particularly preferred. The barcode sequences are designed in order to be able to identify the separate wells on a plate. Thus, the number of barcodes to be applied to a plate should be equivalent to the number of wells on a plate. The W.ID. sequences are designed to that they differ at least 2 bases between any of them, in order to make them more distinguishable during sequencing, and have about 50% GC content and no internal secondary structures. The exact sequences to be used is not of importance, however the user needs to be able to easily identify the barcode sequences in the subsequent sequencing.

Yet according to the first embodiment, a concentration of the released cDNA may be performed as a step d2) after step d) and before step e) on the pooled samples. This is possible when the RT primer used for the RT in step b) comprises a W.ID.

The above-mentioned first embodiment is optimized for high-throughput drug screening on plates with a larger number of wells, such as 384 well plates, or for instance 1536 well plates.

Figure 2:
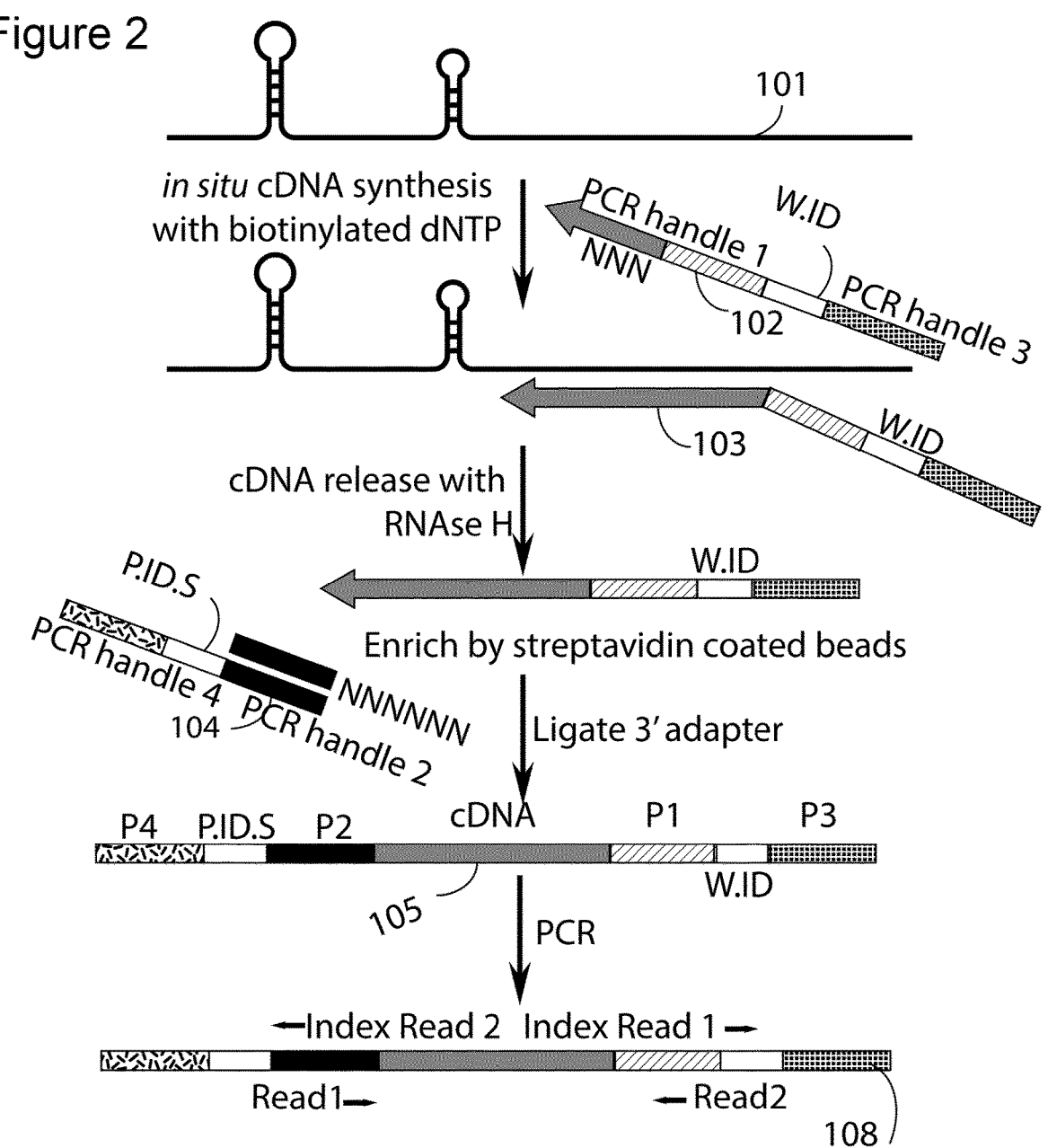

FIG. 2 discloses a simplified cartoon for RIF-Seq method. RNA in-situ was first reverse transcribed with cDNA primers containing (from 5' to 3') a 1st PCR handle1, an identified well ID sequence (W.ID) and random sequence used both as RNA binding sequence and also as unique molecule identifier (UMI). During the reverse transcription, biotin-modified nucleotides are added to be incorporated into the cDNA, to allow cDNA purification and sample concentration with streptavidin coated magnetic beads. The purified cDNA are ligated with double stranded DNA adapters with 3' overhangs to obtain cDNAs extended with PCR handle 2. The ligated products are amplified with using 1st PCR handle 1 and 1st PCR handle2 complementary primers. The PCR products are extended in another round of PCR using primers containing 5'→3' 2nd PCR handle3 (or 4), plate ID sequence 1 (or 2) and 1st PCR handle 1 (or 2) complementary sequences. The final products can be amplified by PCR handle 3 and 4 complementary primers before sequencing.

According to a second embodiment of the method above, a concentration of the PCR handle-containing cDNA is performed as a step e2) after step e). In this embodiment, the samples have not yet been pooled and are still separated, and so the concentration is performed on every single sample.

Figure 3:
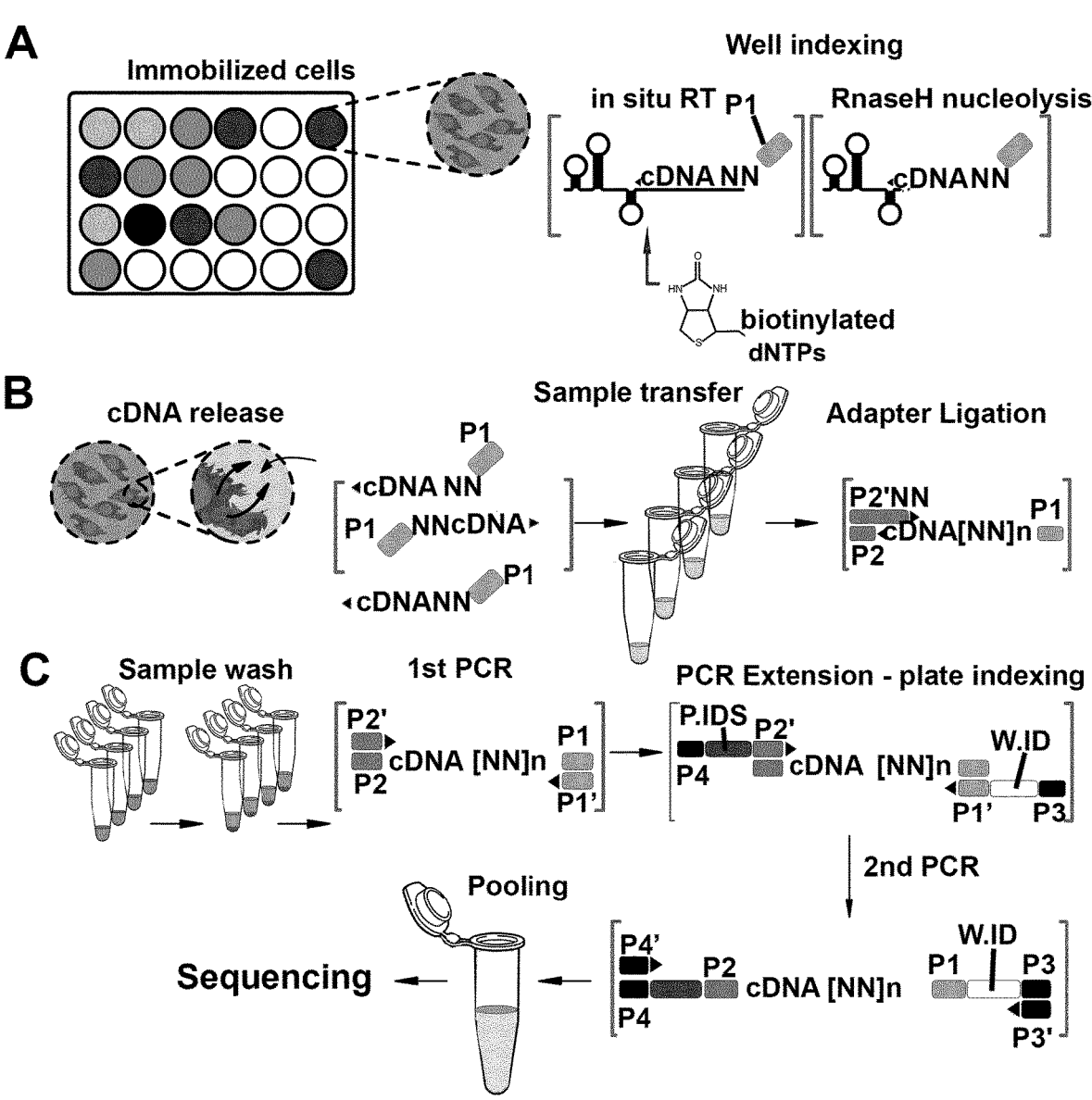
FIG. 3. Example of protocol according to a second embodiment of RIF-Seq. A. Cells used in the experiment are immobilized are fixed. A common RT mix, containing RT primers composed 5'-3' of PCR handle (P1) and random decamer sequence (NN), and partially biotinylated dNTP is dispensed into each well. After RT, cells are washed and RNAseH is added to degrade RNA. B. cDNAs are released passively into supernatant and supernatants are transferred into individual tubes. Sequencing libraries are generated. Adapters, composed of shorter fragment with PCR handle 2 (P2) and longer fragment composed of P2-complementary sequence and degenerate 3' (NN) are ligated 3' to the cDNAs leaving a cDNA insert flanked with 1st PCR handles P1 and P2. C: Magnetic beads are added, cDNAs are captured on beads and purified. cDNAs are amplified by PCR. E: Depending on the experiment scale, samples can be barcoded according to wells, or plates if desired. Finally, sequencing libraries are generated in a second PCR reaction by using P3/P4 PCR handle complementary primers.

FIG. 3 discloses a second embodiment of the invention. FIG. 3A shows that the cells are adhered to the surface of the plate and fixated after for instance being subjected to different compound treatments. Thereafter an in situ, whole transcriptome cDNA synthesis is performed using biotinylated dNTPs, followed by in situ mRNA nucleolysis from the cDNA/RNA duplexes, using RNAseH. In FIG. 3B, cDNA is passively released and diffused out of the cells and into the supernatant. After transferring samples to individual tubes, adapter is ligated to all cDNAs, still well-separated, 3' of the cDNA molecules. In FIG. 3C streptavidin coated magnetic beads are added to each sample so that the cDNA will bind to said beads. Any excess of adapter is removed, and thereafter the sample is concentrated, cDNAs are separated from the beads using proteinase, and the beads discarded. Thereafter a 1$^{st}$ PCR is performed for cDNA amplification, followed by a well and plate indexing PCR extension step. Thereafter, a 2$^{nd}$ PCR for amplification is performed whereby a cDNA library is generated. After the 2$^{nd}$ PCR, all individual samples may be pooled for a simpler and cost efficient sequencing.

FIG. 6A discloses a simplified reaction scheme according to a further embodiment that is also presented in FIG. 4C. mRNAs are reverse-transcribed using RT primers extended with a well (or plate) specific barcode and a PCR handles. After RT, adapters with a well (or plate) specific barcode are ligated to cDNAs that are already extended with the well (or plate) specific barcode. After ligation, full length sequencing libraries can be PCR amplified before sequencing.

Pooling of samples may be performed by pipetting, such as robotic pipetting or manual pipetting. Pooling may also be performed by using reverse centrifuging to collect all the liquid into one large container. The latter is appropriate when the samples may be pooled together as the RT primer comprised a W.ID.

The choice of whether to concentrate the samples as a step d2), or as a step e2), is very much dependent on the type of samples that are analyzed. For testing at a large scale, with multiple samples, it may be preferable and more time- and cost efficient to perform a concentration on a pooled volume of samples as a step d2), where all samples already comprise their own individual W.ID. For a testing at a lower scale, with single or a smaller number of samples, it is appropriate to concentrate as a step e2).

Concentration is preferably performed using streptavidin coated magnetic beads. It is also possible to use streptavidin coated wells, or biotinylated dNTP-independent size separation. It is further also possible to use concentration methods such as size selection columns or other size selection methods. However, due to the fact that biotinylated dNTPs were used in the RT, the cDNA produced by said biotinylated dNTPs will bind to the streptavidin. Streptavidin is a protein that has remarkable affinity to a biotin protein, approximately in a 1:4 ratio.

Additionally, magnetic beads also have a "native" affinity to single stranded DNA, where said "native" affinity increases with cDNA length. Both of these factors, the streptavidin:biotin binding and native affinity to long cDNAs, in combination favors cDNA concentration using attachment to streptavidin coated magnetic beads. Unwanted adapter-RT primers ligation products can be formed if RT primers from the step b) are not completely removed before the cDNA release. However, cDNA will preferably bind to magnetic particles and the majority of any adapter/primer dimers will remain in the solution and thus be removed during the concentration step. Once the concentration has been performed, and unbound dimers in the solution removed, a proteinase is added to release the single-stranded cDNA. The skilled person is well aware of how to use magnetic beads and the protocols for using them in a concentration process.

According to a preferred embodiment, the method further comprises the step f) of a first amplification of the PCR handle-containing cDNAs from step e), in order to obtain a first product mix. At this point the samples will have been concentrated, whether it is as a step d2 or a step e2. Said first amplification is performed with a PCR reaction, using primers that are complementary to PCR handle 2 and PCR handle 1. The PCR performed is a normal PCR reaction, and the skilled person is able to perform this reaction according to standard protocols. Thus, an amplified amount of cDNA has been obtained, facilitating subsequent procedures or method steps.

According to a further embodiment, the method further comprises the steps of g) performing a PCR extension step using indexing primers comprising a PCR handle 3 or a PCR handle 4. The 3' end of the indexing primers are complementary to the 5' PCR handle 1 and 3' PCR handle 2, respectively. Primer extension equips cDNAs with PCR handle 3 and 4, henceforth called a second product mix, and h) a second PCR extension or amplification of the second product mix obtained in step g) using PCR primers complementary to the PCR handles 3 and 4 in order to obtain a third product mix.

In step g), the indexing primer comprising the PCR handle 3 on 5' end will hybridize to the sequence of PCR handle 1, and the indexing primer comprising the PCR handle 4 on 5' end will hybridize to the sequence of PCR handle 2. At least one of the indexing primers in step g) will furthermore comprise at least one Plate Indicating Sequence (P.ID.S). P.ID.S may be chosen depending on the sequencing platform used. For instance, the P.ID.S used for the Illumina® sequencing devices may be used, compatible with Illumina® sequencers such as MiSeq™, NextSeq 500™, or NovaSeq™. However, for customized sequencing protocols or platforms, the P.ID.S may not be required or should be adapted to particular sequencing system, and the skilled person is capable of determining if and which sequences to be used in each particular case. Preferably, only one or two PCR cycles will be performed as the invention with this step is only for extension and indexing of the cDNA with the additional at least one P.ID.S per cDNA molecule, however more than two cycles is also possible. Multiple-cycle amplification using said primers could lead to undesired PCR artefacts due to long size of said primers, and therefore it may be desirable to keep the number of cycles low. The P.ID.S is designed according to the same principle as the W.ID. They may thus comprise 1-50 nucleotides, preferably 5-30, more preferably 5-20, even more preferably 5-15 and most preferably 8-10 nucleotides. 8 nucleotides is particularly preferred. The sequences are not random and are designed in order to be able to identify plates. The P.ID.S. sequences are designed to that they differ at least 2 bases between any of them, in order to make them more distinguishable during sequencing, and have about 50% GC content and no internal secondary structures. The exact sequences to be used is not of importance, however the user needs to be able to easily identify the barcode sequences in the subsequent sequencing. Preferably, only one or two PCR cycles will be performed as the invention with this step is only for extension and indexing of the cDNA with the additional at least one P.ID.S per cDNA molecule, however more than two cycles is also possible. Multiple-cycle amplification using said primers could lead to undesired PCR artefacts due to long size of said primers, and therefore it may be desirable to keep the number of cycles low. The P.ID.S is designed according to the same principle as the W.ID. They may thus comprise 1-50 nucleotides, preferably 5-30, more preferably 5-20, even more preferably 5-15 and most preferably 8-10 nucleotides. 8 nucleotides is particularly preferred. The sequences are not random and are designed in order to be able to identify plates. The P.ID.S. sequences are designed to that they differ at least 2 bases between any of them, in order to make them more distinguishable during sequencing, and have about 50% GC content and no internal secondary structures. The exact sequences to be used is not of importance, however the user needs to be able to easily identify the barcode sequences in the subsequent sequencing.

As will be evident to the skilled person, the number of W.ID. sequences needed exceeds the number of P.ID.S needed, in order to perform the method of the present invention.

In step h) PCR primers that are complementary to the PCR handle 3 and PCR handle 4, respectively, are used to amplify the complete sequencing libraries. By saturating the PCR reactions, the final library products from different plates can be brought to equal amounts. With the third product mix obtained through step h), the cDNA library has been obtained. Said cDNA library may subsequently be used for sequencing according to any method known to the skilled person.

With the first embodiment of the method as described above, indexing primers are used in step g) comprising plate indicating sequences (P.ID.S.), wherein said P.ID.S is a first P.ID.S on the 3' primer and a second P.ID.S on the 5' primer. Thus, the cDNA is extended with specific plate indicators.

With the second embodiment of the method as described above, indexing primers are used in step g) comprising a P.ID.S on either the 3' or 5' primer and/or a well specific barcode sequence (W.ID) on either the 3' or 5' primer. After an amplification or extension according to step h), the third product mix may thereafter be pooled, as they are now indexed for both well and plate.

After step g), all samples may be pooled as the sequencing will identify the cDNA sequences that comprise the specific W.ID and P.ID.S incorporated during any of the preceding steps in the method.

According to another embodiment of the present method, the RT primer in step b) may further comprise a P.ID.S and a PCR handle 3, and the adapter molecule in step e) may further comprise a W.ID and a PCR handle 4. Alternatively, the RT primer in step b) may further comprise a W.ID. and a PCR handle 3, and the adapter molecule in step e) may further comprise a P.ID.S and a PCR handle 4. With this embodiment, only one PCR amplification needs to be performed, directly after step e. The aim of this embodiment is to decrease the number of PCR steps, whereby a more time efficient method is obtained.

The PCR handle sequences 1-4 may be chosen depending on the sequencing platform that will be used. For instance, the sequences used for the Illumina® sequencing devices may be used, compatible with Illumina® sequencers such as MiSeq™, NextSeq 500™, or NovaSeq™. However, if another sequencing platform is used, the PCR handles should be adapted to that particular platform, and the skilled person is capable of determining the sequences to be used in each particular case.

By performing the method according to any of the embodiments above by using a RNAseH in the release mix for releasing the single-stranded cDNA, as mentioned above, the cDNA will be released from unlysed cells. Once the supernatant comprising the single-stranded cDNA has been removed, these cells may thus be the subject to downstream procedures such as immunochemistry, cell paining, hematoxylin-eosin staining, brightfield imaging or any other imaging technique that the user wishes to perform on the cells from which the cDNA library has been generated.

The method and any of the embodiments thereof may be performed as a manual process or an automated process. Thus, manual pipetting may be used in the method, or an automated process using a robot for performing all the steps may also be used. Thus, the method is flexible and may be used as appropriate for a user.

The skilled person will be able to determine the sequences that should be used for the primers in order for them to be complementary to the PCR handles. The exact sequence for these is not important for the inventive concept of the present disclosure.

EXAMPLES

The invention will now be described by way of examples that are not intended to limit the scope of the invention, but are included in order to illustrate and exemplify certain aspects and features of the invention.

Example 1

Using barcoded random decamers—as primers—and biotinylated dNTPs, RNAs are reverse transcribed (RT) inside fixed cells in separate wells (FIG. 1, 2). By using barcodes in RT reaction, different wells can be spatially encrypted in a plate or in different tissue regions. Importantly, rRNAs natively existing in structured forms or ribonucleoprotein complexes are not participating in RT and do not require exclusion at the later steps. Biotinylated dNTPs are incorporated in a newly synthesized cDNA strand for a later purification step using streptavidin coated magnetic beads. After RT, cells are washed to remove excess of RT primers. cDNAs are retrieved from RNA/cDNA heteroduplexes using RNAseH ribonuclease and supernatants from all wells are pooled in a single, larger single volume. Importantly, fixed cells are not exposed to any lytic chemicals during this protocol. Preservation of protein epitopes allows the user to spear plates and used cells in downstream procedures like immunochemistry, cell paining, (Bray et al., 2017; Sakaue-Sawano et al., 2008; States et al., 2013), hematoxylin-eosin staining or brightfield imaging. cDNAs are concentrated on the surface of streptavidin-coated magnetic beads and 5' adapters are ligated 3' from the extended cDNA end using T4DNA Ligase. At this point of the protocol, cDNAs are flanked with two 3' and 5' $1^{st}$ PCR handles and libraries can be amplified by PCR using primers complementary to the sequences embedded in the PCR handles. In the next step—depending on the scale of the experiment—cDNA libraries are extended with plate-specific indexes and $2^{nd}$ PCR P3 or P4 handle sequences, compatible with widely present Ilumina Sequencers. Extended sequencing libraries are amplified in a second PCR reaction before sequencing.

Example 2

Figure 4:
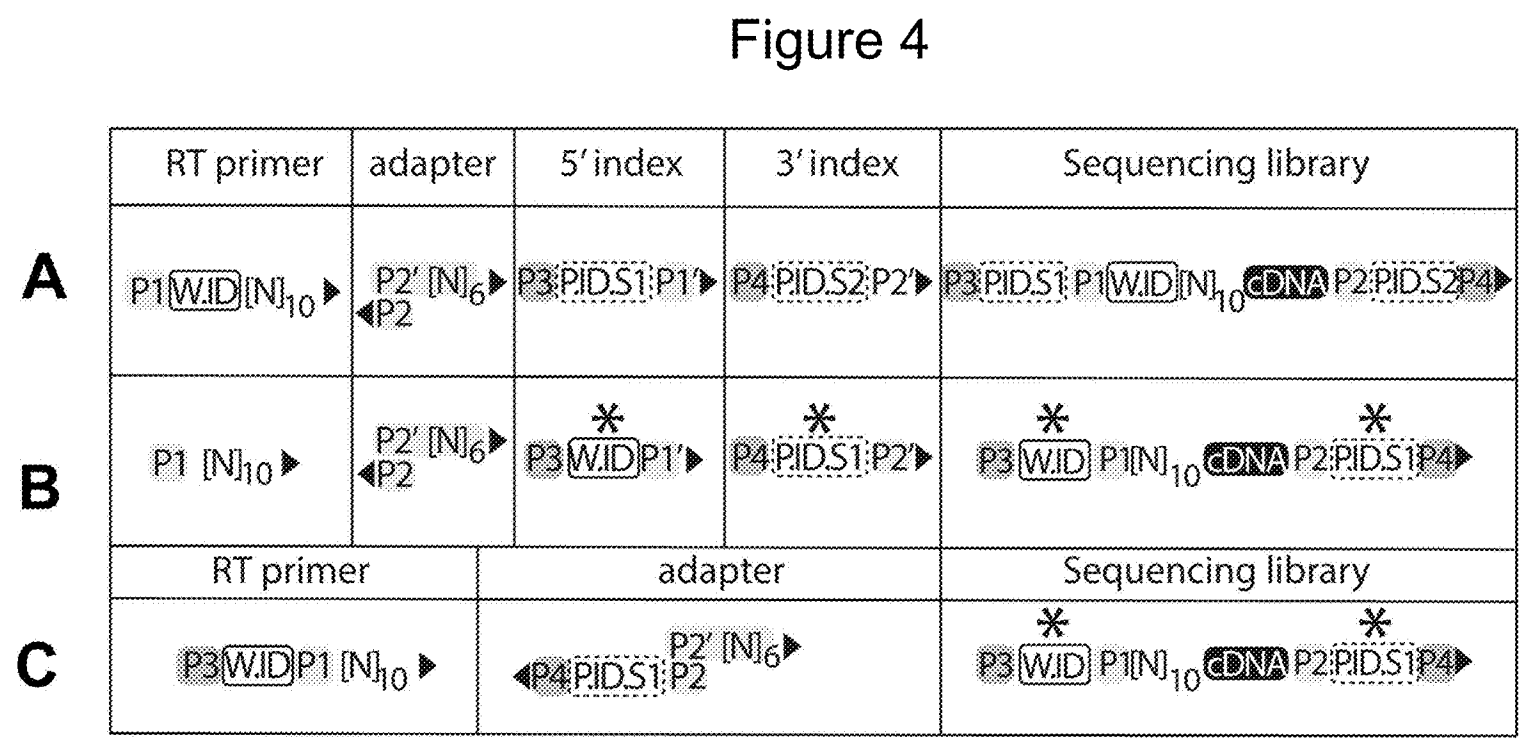

RIF-Seq protocol is very scalable, and can be used for single reactions, 96/384/1536 well plates, or tissue samples. RIF-Seq can also be performed on various materials, such as cultured cells, tissue sections, tissue microarrays, or TMAs. Example 1 above is optimized for high-throughput drug screening on 384 well plates although the method can be adapted to 1536 well plates. With the present Example, RIF-Seq method can be easily performed on a much smaller scale, including a single or a just a few wells or tissue sections. In the present example, if a lower scale experiment is desired, an identical RT reaction mix is introduced into all wells. Since wells receive the same reaction components, RT primers do not contain well-specific barcodes but PCR handles alone (FIG. 3, FIG. 4B). The RT reaction is conducted with biotinylated dNTPs, mRNAs are reverse transcribed (RT) inside fixed cells in separate wells. rRNAs natively existing in structured forms or ribonucleoprotein complexes are not participating in RT and do not require exclusion at the later steps. Biotinylated dNTPs are incorporated in a newly synthesized cDNA strand for a later purification step using streptavidin coated magnetic beads. After RT, cells are washed to remove excess of RT primers. cDNAs are retrieved from mRNA/cDNA heteroduplexes using RNAseH ribonuclease and supernatants. In this step, a common release mix can be applied to all wells simultaneously. Such a format limits the number of enzymatic reactions that needs to be performed. Just like for the Example 1, fixed cells are not exposed to any lytic chemicals during the protocol. Preservation of protein epitopes allows the user to spear plates and used cells in in downstream procedures like immunochemistry, cell paining, (Bray et al., 2017; Sakaue-Sawano et al., 2008; States et al., 2013), hematoxylin-eosin staining or brightfield imaging. Supernatants from the wells are transferred into smaller tubes (PCR tubes are preferred) and cDNAs inside the supernatants are concentrated on the surface of streptavidin-coated magnetic beads and 5' adapters are ligated 3' from the extended cDNA end using T4DNA Ligase. Same ligation mix is applied at this point. cDNAs become flanked with two $1^{st}$ PCR handles P1, P2 and cDNAs can be amplified by PCR using primers complementary to the PCR handles. In the next step—depending on the scale of the experiment—cDNA libraries may be extended with well (W.ID) and/or plate-specific indexes (P.ID.S) and $2^{nd}$ PCR P3 or P4 handle sequences, compatible with widely present Ilumina Sequencers. Exact placing of well or plate indexes (whether either is present on the 3' or 5' extremity of the sequencing library) is not important and can be chosen (FIG. 4). Extended sequencing libraries are amplified in a second PCR reaction, and finally, samples are pooled together before sequencing.

Example 3—Components of RT Primers and Positioning of Sequences in Sequencing Libraries As described above in Example 1, cDNAs from individual wells can be barcoded by using unique RT primers. Dispensing of primers can be done automatically and then, common RT mix can be dispensed into all wells simultaneously. After ligation of a common 3' adapter, pooled cDNAs can be further indexed with plate-specific sequences (FIG. 4A). If the experiment is performed according to description in Example 2, samples are not pooled until the end of the procedures. Samples receive the same RT primers and the same adapters. During the library extension step, where samples where indexed with plate-specific sequences in Example 1, samples can be well- and plate-indexed depending on the experiment scale and the users choosing. Well- and plate indexes can be positioned on either side of the sequencing library (FIG. 4B). At the level of the full sequencing library, first and second embodiment differ by the sample barcode position. It is localized between P1/2 PCR Handle sequences (Example 1) or between P1/P3 and P2/P4 sequences on either 375' end of the library (Example 2).

Figure 6:
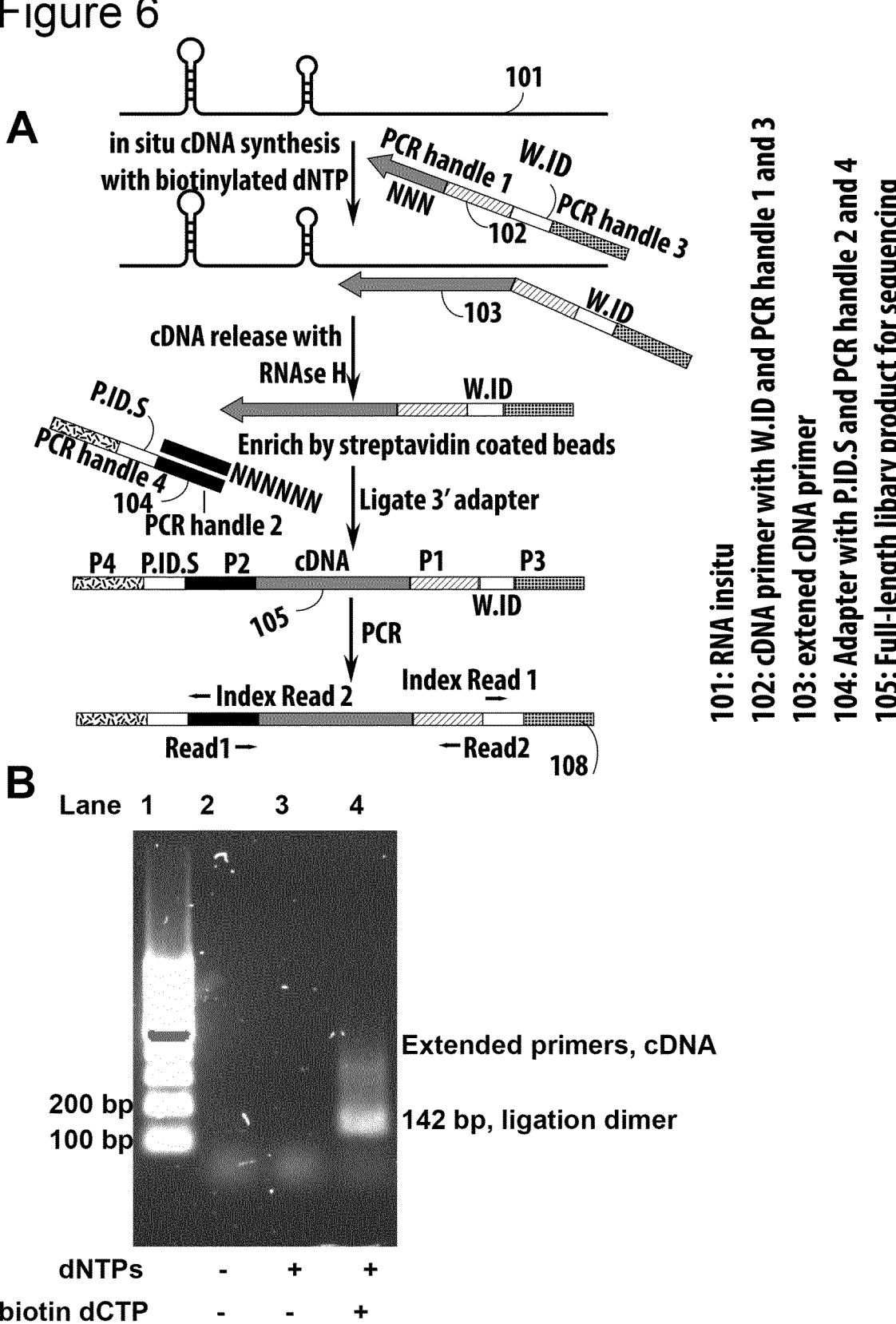
FIG. 6. A: Simplified cartoon of RIF-Seq approach presented in the FIG. 4C. 101: RNA in situ. 102: cDNA primer with W.ID and PCR handle 1 and 3. 103: extended cDNA primer. 104: Adapter with P.ID.S and PCR handle 2 and 4. 105: Full length library product for sequencing. B: The adapter ligated cDNA (lane 4) was amplified by PCR. The PCR products were analyzed by agarose gel electrophoresis stained with sybrgreen to visualize the DNA bands. The DNA ladder (lane 1) was included to indicate the length of bands. The ligation dimmer or 142 bp is visible in lane 4 as well as a characteristic DNA smear representing successful cDNA library amplification.

Well- or plate-specific sequences can be added via polymerase extension like in Examples 1 or 2 (FIG. 4A, 4B). To decrease the number of PCR steps, well- or plate-specific sequences can be also introduced by using RT primers and ligation adapters that are already equipped (extended) with these sequences (FIG. 4C, FIG. 6). In this approach, well- or plate-specific sequence can be put in either RT primer or 3' ligated adapter depending on the experimental setup and user's choosing.

Example 4—Optimization of In Situ cDNA Synthesis and Purification Step

Figure 5:
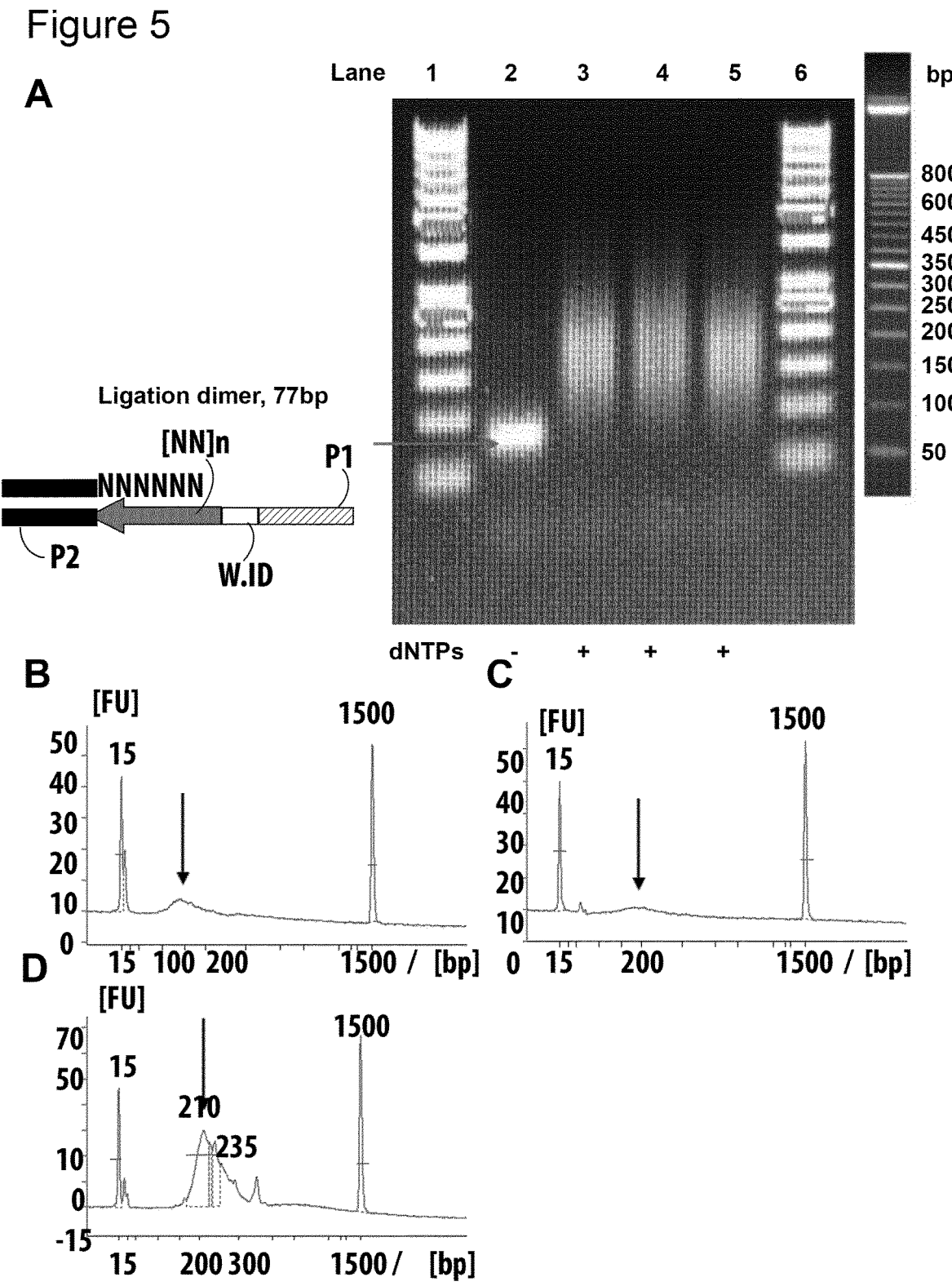

In separate reactions, the cDNA synthesis mix was prepared with or without dNTP. The inventors found the length of PCR products without dNTP equal to the size as cDNA primer plus P2 adapter (79 bp), while in the reactions where dNTP was included, the PCR products showed a distribution of different lengths, longer than the adapter plus cDNA primer, indicating a successful cDNA synthesis (FIG. 5, lane 3-5).

Figure 7:
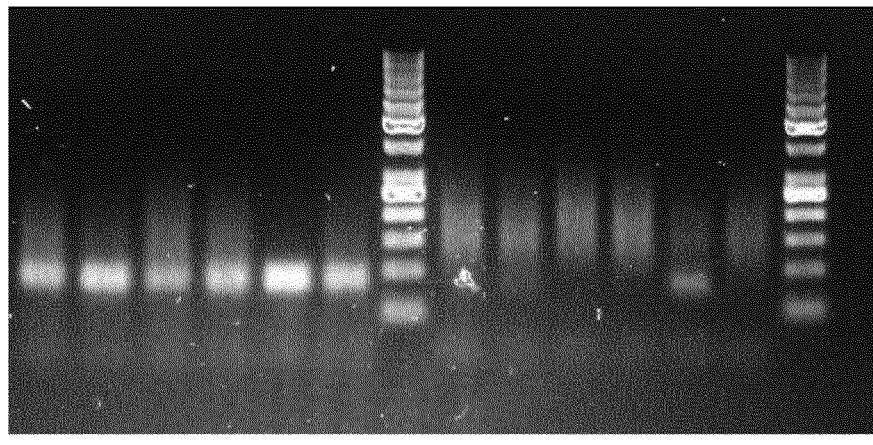
FIG. 7. The released cDNA (containing biotinylated nucleotides) was either purified with streptavidin coated magnetic beads (lane 8-13) or not (lane 1-6), before PCR amplification. The ladder (lane 7,14) was included to indicate the size of the PCR products. Strong primer-dimer bands are visible when purification was not performed.

The inventors also tested if the cDNA purification is necessary. After releasing the cDNA from the wells and adapter ligation, the inventors performed the PCR either with or without purification using streptavidin beads. Where magnetic beads purification step was omitted, the inventors observed that majority of the PCR products where the primer-adapter dimers (FIG. 7, lane 1-6). After purifying cDNAs on magnetic beads and removing primer-adapter dimers, a majority of amplified products were the extended cDNAs (FIG. 7, lane 8-13).

Figure 8:
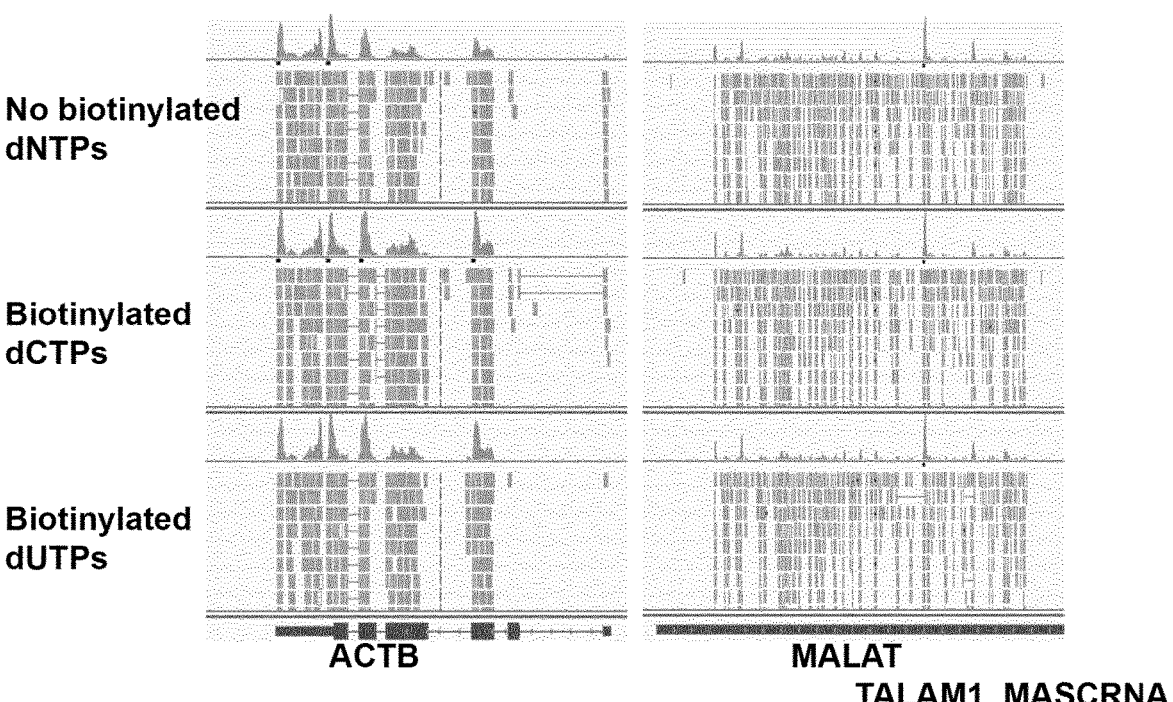
FIG. 8. RT reactions were conducted without biotinylated dNTPS or with biotinylated dCTPs and biotinylated dUTPs. The sequencing reads were mapped to human RNA database, ACTB gene and a MALAT1, TALAM1, MASCRNA ncRNAs are shown as references. Alignment of reads (boxes) is shown against thicker reference lines (exons) and thinner lines (introns) on the panel below. Grey peaks above aligned reads are representing higher density of sequencing reads.

Purification of cDNAs is possible due to the presence of biotinylated nucleotides that were present in the RT reaction. The inventors tested if biotin residue-conjugated nucleotides could introduce bias during sequencing and consequently, mapping of cDNAs to the reference RNA database. The inventors found the biotin dCTP, biotin dUTP and no biotin yield similar cDNA coverage on the reference RNA database (FIG. 8).

Example 5—RIF-Seq Performance

Figure 9:
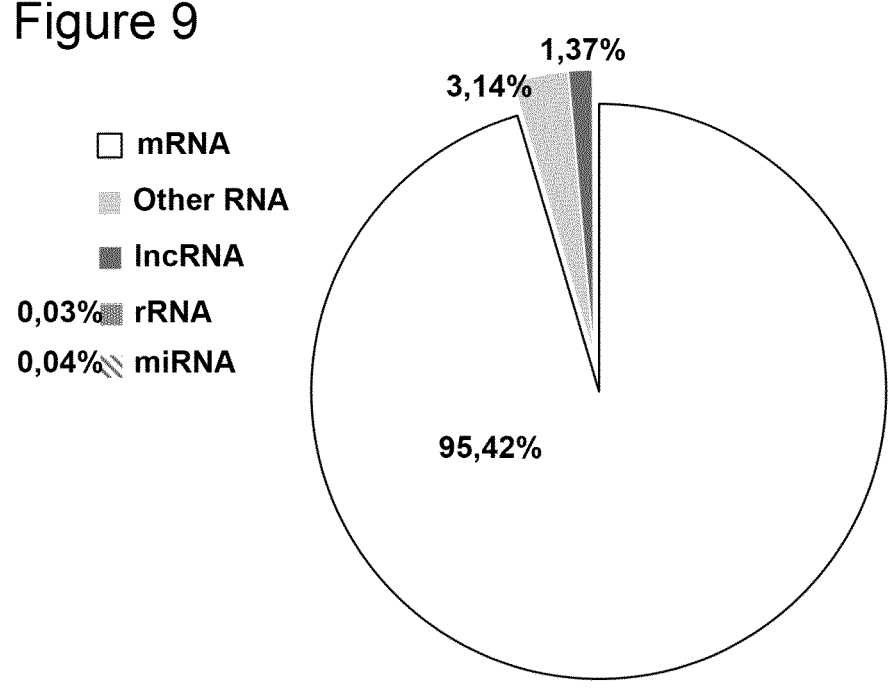
FIG. 9. The sequencing reads were mapped to human RNA database. The ratios of different mapped RNA species were indicated.
Figure 10:
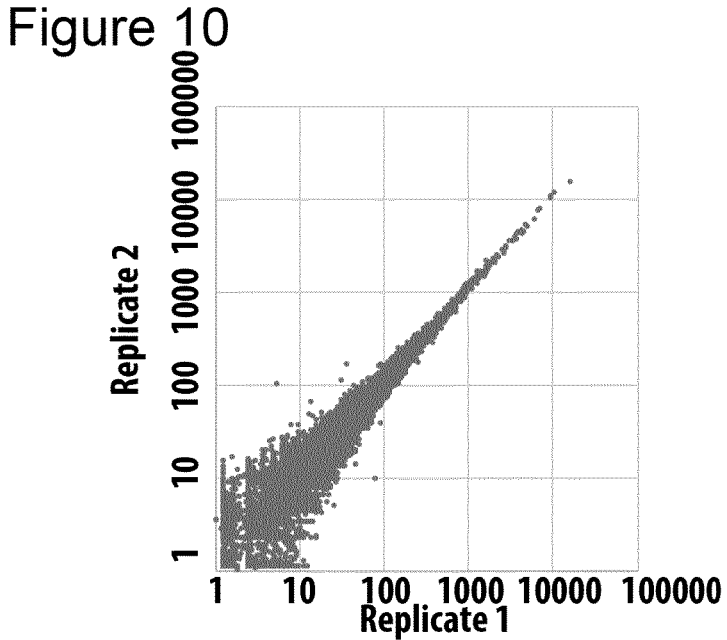
FIG. 10. The sequencing read count per million reads (CPM) were used to calculate the gene expression reproducibility of two samples (replicate_#1 and replicate_#2).

After sequencing, the inventors aligned the sequencing reads against the reference RNA database and calculated the percentage of different species of RNA (FIG. 9). The inventors found that the majority of mapped reads were indeed mRNA and a low percentage of other non-coding RNA but very few rRNA. The inventors hypothesized that the rRNA is heavily folded in the fixed cells, which makes them a difficult target for in situ reverse transcription. The inventors also compared two independent experiments of RIF-Seq, and found the results were very reproducible (FIG. 10)

Figure 11:
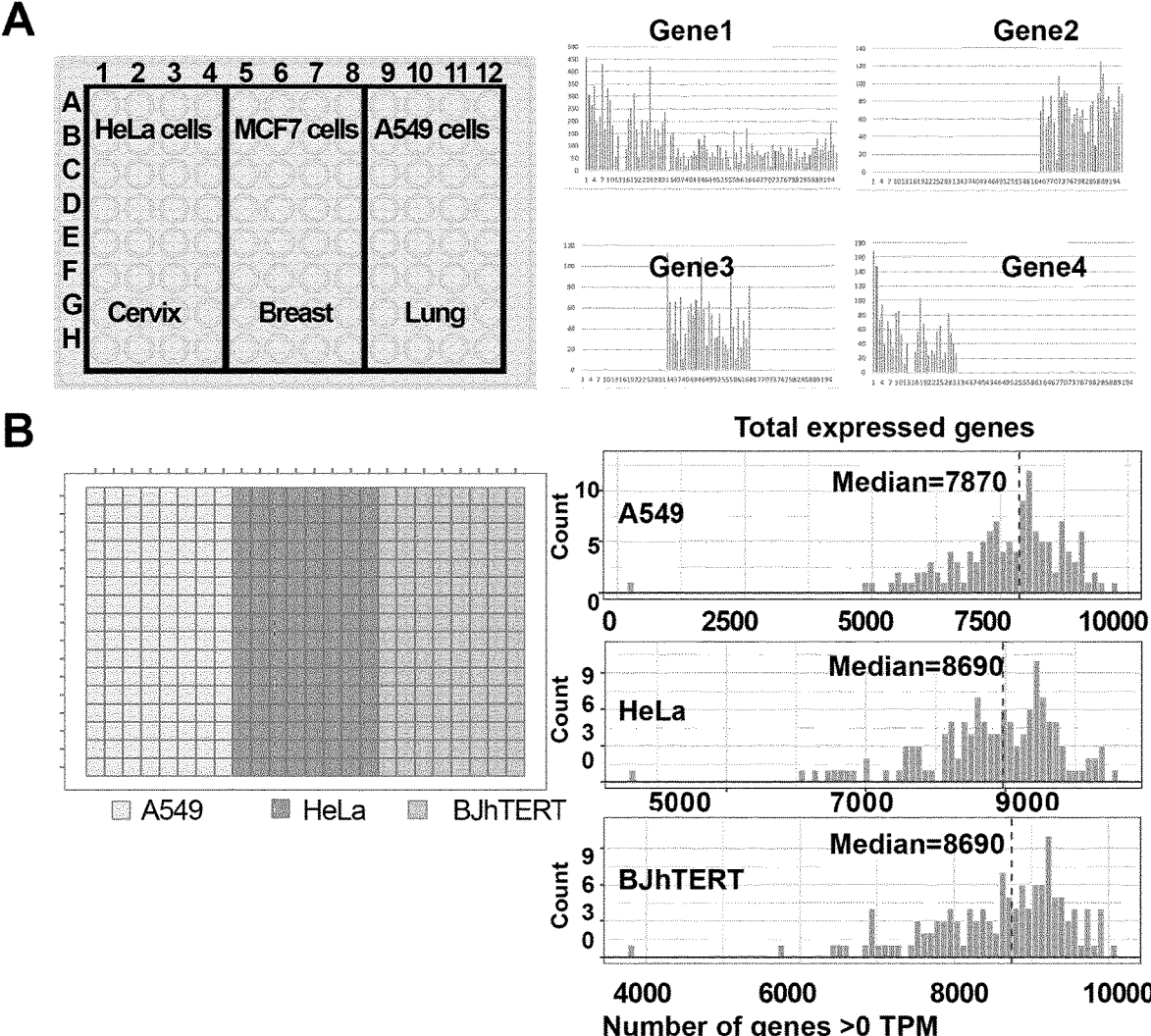
FIG. 11. A: Upper panel: RIF-Seq using a set of 384 barcodes (4 barcodes per well) on 3 different cell lines in a 96-well plate (each cell line was present in in 32 wells) according to the plate schematic. Lower panel: expression of selected genes (Gene 1-4, y-axis) is presented for all wells in the x-axis. Housekeeping gene 1 is expressed in all cells while other genes are selectively expressed for other cell types.

Example 6—Validation of RIF-Seq Using 3 Different Cell Lines Cultured in 96 and 384 Well Plates As a proof of concept to demonstrate RIF-Seq can be used as a high-throughput method for whole transcriptomics analysis, the inventors cultured A549, HeLa and MCF-7 cell lines on the 96-well plate and A549, HeLa and BjHTERT cell lines on 384 well plate. Each cell line was present in either 32 (96 well plate) or 128 wells (384 well plate). Then the inventors performed the RIF-Seq using a set of 384 barcodes where either 4 barcodes were used per well (in 96 well plate) or individually (in 384 well plate). After sorting the reads according to the different well-barcodes, the inventors identified the gene expression from cells in different wells. Some housekeeping genes (Gene1) are universally expressed on all 3 cell types, while some genes are only expressed on 1 cell line (FIG. 11A). This result suggests that RIF-Seq can be used to identify biomarker genes, characteristic to cell lines of different origin. Then the inventors performed a T-distributed Stochastic Neighbor Embedding (t-SNE) analysis using the gene expression. The inventors could clearly identify three clusters of cells, as expected (FIG. 12A). In all cell lines analyzed in 384 well plate, median number of detected genes was between 7800-8700 with normal distribution (FIG. 11B). PCA analyses of cell lines cultured in 384 plate showed distinct clustering of cell groups based on their gene expression correlation (FIG. 12B).

Example 7—RIF-Seq for Spatial Transcriptomics Analysis

Figure 13:
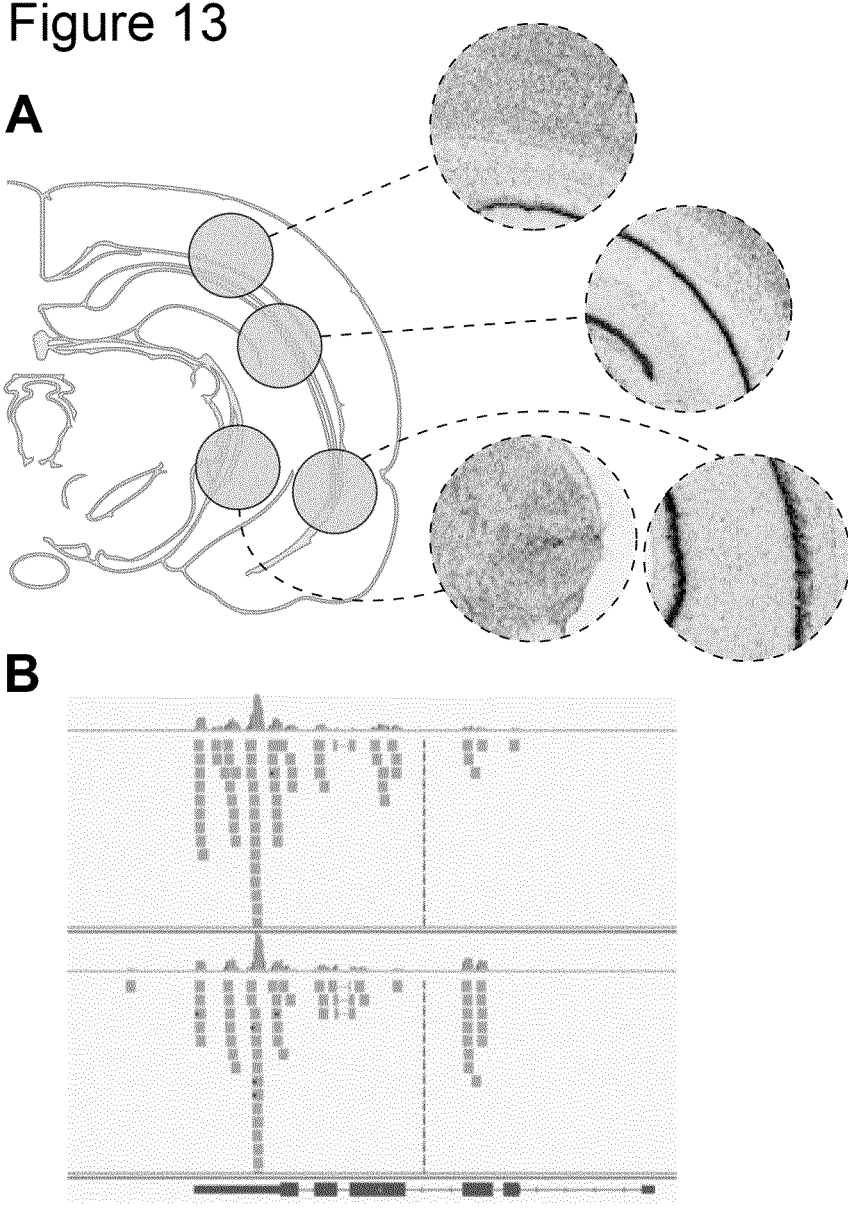

Spatial transcriptomics analysis is a very powerful way to investigate tissue heterogeneity. The current methodologies either perform the detection of RNA (with or without reverse transcription) directly on tissue or releasing RNA molecules to a DNA microarray, where each spot immobilized with oligonucleotides in the size of hundreds of micrometres, captures the RNA molecules vertically therefore preserving the spatial information. In the present example, researchers propose an alternative way by allowing reverse transcription (RT) mixture with different and designed barcodes to different parts of a tissue followed by in situ reverse transcription and then pooling all the cDNA together followed by library preparation and sequencing. By analysing the cDNA sequence and the barcodes, the transcriptomic profiling in each part can be revealed. The resolution is deponent of the area of each RT mixture can contact on the tissue. By using a common 1-2.5 µl pipette, sub millimetre can be achieved (FIG. 13-14). To avoid evaporation of RT mixture during prolonged in situ reverse transcription (2-4 hours), the tissue can be first dehydrated and covered by oil phase and then the RT mixture is added onto the tissue, which is then preserved between the tissue and the oil. By including DNA staining reagent, e.g. DAPI, the cells covered by the droplet of RT mixture can be recorded by microscope (FIG. 13-14).

Example 8—Using RIF-Seq to Reveal
Drug-Induced Biological Effects and Prediction of
Drug Mechanisms of Action in High-Throughput
384 Well Plate Format To evaluate if RIF-Seq can be used to detect changes in gene expression due to action of compounds (drugs) and if gene expression signatures can be used to predict mechanism of action of the compound, the inventors performed screen of two compounds in various concentration (delivered to cells in DMSO) and controls (DMSO alone) in high throughput fashion on automated platforms. A549 cell line was seeded using automatic cell dispenser onto low volume imaging plate to concentration of 2 000 cell per well. After over-night incubation, drugs were manually added to cells according to schematics presented in the FIG. 16A, cells were fixated and RIF-Seq protocol was executed using automated robotic liquid handlers. PCA analyses of compound-grouped samples revealed distinct sample groups that were correlated and differed significantly from DMSO controls. Gradient of differences is presented for vorinostat as example in FIG. 16B. Volcano plot of genes over- and under-expressed upon treatment with vorinostat at 8.3 μM concentration reveal number of genes with significantly altered expression. Using Gene Set Enrichment Analysis (GESA) inventors compared the differential gene expression data of samples treated with 8.3 μM vorinostat and controls and which differently expressed genes are annotated to pre-defined gene sets contained in the Broad Institute "Hallmarks" list (FIG. 16D). According to the analysis, inventors observed down-regulation of the cell cycle and p53 pathways, E2F targets, cell cycle checkpoints and MYC targets, concordant with the public literature.

Example 9—Materials and Methods

Cell Culturing and Fixing

Cells were cultured in T25 and T75 cell culturing flasks at 37° C. under 5% CO2 in RPMI1640 medium (HeLa, BjHTERT, MCF-7) or F12K medium (A549) with 10% complete fetal bovine serum (FBS), penicillin-streptomycin, and glutamine, up to 80% confluency. Before seeding cells into plates, cells were washed with PBS and dislodged using Tripsin-EDTA and resuspended in fresh medium to a concentration of 66 cells/μL. Manually (100 μL volume, 96 well plate) or by using automatic cell dispenser (30 μL volume, 384 well plate) cells were transferred into desired vessels and incubated over-night. For 96 well plates, the cell culture media were removed and plate was washed twice with 100 μl cold PBS in each well. Then 100 μl 3.7% PFA solution was added to each well and incubated at room temperature for 15 min. For 384 well plates, 10 μl of freshly prepared 16% formaldehyde was added to 30 μl of cell media to obtain a final formaldehyde concentration of 3.7%. Fixation was performed for 20 minutes at room temperature. After removing the formaldehyde solution, each well was washed twice with 1×DEPC-PBS and followed by ETOH series (70%, and 99%) washing, each for 2 min. The plates were air dried for 15 min at room temperature and store at −80° C. for further use.

RIF-Seq Library Preparation for 96 Well Plates
According to Example 1

For each reaction, 20 μl RT mix containing 0.5 mM dN(A,T,G,C)TP, 25 μM biotinylated-dCTP, 0.1 mg/ml BSA, 0.4 U/μl RiboLock™ RNase Inhibitor, 10 U/μL reverse transcriptase and 5 μM cDNA primers in 1×RT buffer were added to each well and incubated at 37° C. for 4 h. After removing the RT mix and washing 3 times with DEPC PBS with tween 20 (PBST), 20 μl release mix containing 0.25 U/μl RNAse H in 1× T4 ligase buffer was added to each well to release the cDNA, at 37° C. for 0.5 h. Then the cDNA from all the wells are pooled together. Then T1 beads (ThermoFisher Scientific®, 1:50 ratio as the cDNA release mix) were added to the pooled cDNA and incubated at room temperature for 0.5 h on agitation. After removing the supernatant using a magnet, beads were washed 3 times using PBST. Then 100 μl ligation mix containing 1 mM ATP, 500 nM adapters, 0.05 U/μl T4 ligase was added to the beads and incubated at room temperature for 1 h. Then the ligation mix was removed and washed twice with PBST. Then a release mix containing 2 mg/ml Proteinase K in 1× DreamTag™ DNA buffer was added to the beads to release the cDNA. The reaction was performed at 50° C. for 0.5 h and terminated by heating up to 90° C. for 10 min. The supernatant was collected into a new PCR tube and added with equal volume of PCR mix containing 400 μM dN(A, T,G,C)TP, 1 μM PCR primers, 0.05 U/μl DNA polymerase. The PCR was carried using program as 95° C. for 2 min, then 20 cycles of 95° C., 15 sec, 60° C. 1 min, 72° C. 1 min. Then 0.5 μl of the PCR products were added into another PCR mix containing 200 μM dN(A,T,G,C)TP, 0.025 U/μl DNA polymerase, and 250 nM sample indexing primers. Then a second PCR was performed as 95° C. for 2 min, then 2 cycles of 95° C., 15 sec, 60° C. 1 min, 72° C. 1 min, followed by 72° C. 3 min and hold on 10° C. Then 0.5 μl of the second PCR products were added to the final PCR mix containing 200 μM dN(A,T,G,C)TP (10 mM, Thermo), 1× Sybr green I, 500 nM PCR primers and 0.025 U/μl DNA polymerase. The final PCR was carried as 95° C. for 2 min, then 20 cycles of 95° C., 15 sec, 60° C. 1 min, 72° C. 1 min. Then the PCR products were purified by Qiagen® PCR purification kit. Thereafter the purified PCR products were measured by Qubit dsDNA high sensitivity kit and adjusted to 4 nM for sequencing.

RIF-Seq Library Preparation for 384 Well Plates
According to Example 7

Prior experiment, 384 well primer plate was prepared with 5 μM final concentration of each primer. Primer plate was loaded onto Bravo Automated Liquid Handling Platform (Agilent®) and cell plate was rehydrated with PBS. PBS was removed and, for single 384 well plate, total 1550 μl of 2× RT mix containing 1 mM dN(A,T,G,C)TP, 50 μM biotinylated-dCTP, 0.2 mg/ml BSA, 0.8 U/μl RiboLock™ RNase Inhibitor, 40 U/μL reverse transcriptase in 2×RT buffer were mixed and 3 μl dispensed into each well. Using Bravo, 3 μl of each primer was transferred into cell plate, plate was sealed, spanned and incubated at 37° C. for 4 h in humidity chamber. Plate was washed with total volume of 300 μl PBS-T using automated microplate washer (Thermo Fisher Scientific®). Total of 2700 μl release mix was prepared, containing 0.25 U/μl RNAse H in 1× T4 ligase buffer. Using multidrop microplate dispenser (Thermo Fisher Scientific®), 6 μl of release mix was added into each well to release the cDNA, plate was sealed, spanned and incubated at 37° C. for 1 h in humidity chamber. To increase sample volume, using multidrop microplate dispenser, 4 μl of 1× T4 DNA Ligase buffer was added into each well. Plate was inserted into Bravo and 8 μl of release mix was aspirated from each well and pooled into a new 96 well pooling plate. Pooled volume was transferred into separate 1.5 mL tubes.

Adapter ligation was performed in larger pooled volume in each tube, by adding Ligation mix containing final concentration of 1 mM ATP, 500 nM adapters, 0.25 U/μl T4 ligase. Ligation was performed at 16° C. for 1 hour on agitation. Then T1 beads (ThermoFisher Scientific®, 1:50 ratio as the cDNA release mix) were added to the adapter-ligated cDNA and incubated at room temperature for 1 h on agitation. After removing the supernatant using a magnet, beads were washed 3 times using PBST. To release cDNAs from magnetic beads, a 30 μl mix containing final concentration of 1 mg/ml Proteinase K in 1× DreamTag™ DNA buffer was added to the beads. The reaction was performed at 50° C. for 0.5 h and terminated by heating up to 90° C. for 10 min. The supernatant was collected into a new PCR tube and added with equal volume of PCR mix containing 400 μM dN(A,T,G,C)TP, 1 μM PCR primers, 0.05 U/μl DNA polymerase. The PCR was carried using program as 95° C. for 2 min, then 20 cycles of 95° C., 15 sec, 60° C. 1 min, 72° C. 1 min. To index all cDNAs with plate index, 0.5 μl of the PCR products were added into 9.5 μL PCR mix containing 200 μM dN(A,T,G,C)TP, 0.025 U/μl DNA polymerase, and 250 nM sample indexing primers. Then a second PCR was performed as 95° C. for 2 min, then 2 cycles of 95° C., 15 sec, 60° C. 1 min, 72° C. 1 min, followed by 72° C. 3 min and hold on 10° C. Then 0.5 μl of the second PCR products were added to the final PCR mix containing 200 μM dN(A,T,G,C)TP (10 mM, Thermo), 1× Sybr™ green I, 500 nM PCR primers and 0.025 U/μl DNA polymerase. The final PCR was carried as 95° C. for 2 min, then 20 cycles of 95° C., 15 sec, 60° C. 1 min, 72° C. 1 min. Then the PCR products were purified by Qiagen® PCR purification kit. Thereafter the purified PCR products were measured by Qubit dsDNA high sensitivity kit and adjusted to 4 nM for sequencing.

Data Analysis

After sequencing, the bcl2fastq was first used to demultiplex the reads originated from different indexes (from different plates). From each plate, reads were demultiplexed per-barcode and barcode sequence was removed from reads. Read quality as rRNA proportions were assessed using publicly available software. Transcript expression, gene expression and quality were measured using tailormade scripts. Finally, differential expression and clustering was performed using public software and tailormade scripts.

REFERENCES

Bray, M., Singh, S., Han, H., Davis, C. T., Borgeson, B., Hartland, C., . . . Carpenter, A. E. (2017). Cell Painting, a high-content image-based assay for morphological profiling using multiplexed fluorescent dyes Mark-Anthony, 11 (9), 1757-1774. https COLON SLASH SLASH doi.org/10.1038/nprot.2016.105.Cell Bush, E. C., Ray, F., Alvarez, M. J., Realubit, R., Li, H., Karan, C., . . . Sims, P. A. (2017). PLATE-Seq for genome-wide regulatory network analysis of high-throughput screens. Nature Communications, 8 (1). https COLON SLASH SLASH doi.org/10.1038/s41467-017-00136-z Chomczynski, P., & Sacchi, N. (1987). Single-step method of RNA isolation by acid guanidinium thiocyanate-phenol-chloroform extraction. Analytical Biochemistry, 162, 156-159. https COLON SLASH SLASH doi.org/10.1006/abio.1987.9999

Lao, K. Q., Tang, F., Barbacioru, C., Wang, Y., Nordman, E., Lee, C., . . . . Surani, M. A. (2009). mRNA-sequencing whole transcriptome analysis of a single cell on the solid™ system. Journal of Biomolecular Techniques, 20 (5), 266-271. https COLON SLASH SLASH doi.org/10.1038/nmeth.1315

Ramsköld, D., Luo, S., Wang, Y. C., Li, R., Deng, Q., Faridani, O. R., . . . Sandberg, R. (2012). Full-length mRNA-Seq from single-cell levels of RNA and individual circulating tumor cells. Nature Biotechnology, 30 (8), 777-782. https COLON SLASH SLASH doi.org/10.1038/nbt.2282

Sakaue-Sawano, A., Kurokawa, H., Morimura, T., Hanyu, A., Hama, H., Osawa, H., . . . Miyawaki, A. (2008). Visualizing Spatiotemporal Dynamics of Multicellular Cell-Cycle Progression. Cell, 132 (3), 487-498. https COLON SLASH SLASH doi.org/10.1016/j.cell.2007.12.033

States, C., Gustafsdottir, S. M., Ljosa, V., Sokolnicki, K. L., Wilson, J. A., Walpita, D., . . . Shamji, A. F. (2013). Multiplex cytological profiling assay to measure diverse. PLOS ONE, 8 (12), 1-7. https COLON SLASH SLASH doi.org/10.1371/journal.pone.0080999

Subramanian, A., Narayan, R., Corsello, S. M., Peck, D. D., Natoli, T. E., Lu, X., . . . . Golub, T. R. (2017). A Next Generation Connectivity Map: L1000 Platform and the First 1,000,000 Profiles. Cell, 171 (6), 1437-1452.e17. https COLON SLASH SLASH doi.org/10.1016/j.cell.2017.10.049

Ye, C., Ho, D. J., Neri, M., Yang, C., Kulkarni, T., Randhawa, R., . . . Kaykas, A. (2018). DRUG-seq for miniaturized high-throughput transcriptome profiling in drug discovery. Nature Communications, 9 (1), 1-9. https COLON SLASH SLASH doi.org/10.1038/s41467-018-06500-x

The invention claimed is:

1. A method of forming complementary DNA (cDNA) sequencing libraries from RNA *in situ* comprising steps of:
   (a) fixating intact cells, immobilized on a solid surface;
   (b) performing an in situ reverse transcription (RT) inside the intact cells, using RT primers comprising a 5' PCR handle 1, and deoxynucleotide triphosphates (dNTPs), wherein the dNTPs include biotinylated dNTPs;
   (c) releasing single stranded cDNA from the intact cells using a release mix, wherein the release mix comprises an RNAse, such that the single stranded cDNA is released from intact cells without lysing the intact cells;
   (d) collecting a supernatant comprising released cDNA into a single volume or in separate volumes; and
   (e) introducing, by ligation or polymerase extension, an adapter molecule comprising a 3' PCR handle 2 that will bind 3' of the cDNA.

2. The method according to claim 1, wherein the intact cells are eukaryotic cells of human or non-human origin, or the intact cells are prokaryotic cells of bacteria or archaea domain.

3. The method according to claim 1, wherein the immobilization of intact cells to the solid surface occurs spontaneously.

4. The method according to claim 1, wherein the immobilization of intact cells to the solid surface occurs by gravity or pressure-induced forces, for intact cells present in liquid suspension.

5. The method according to claim 1, wherein the immobilization of intact cells to the solid surface occurs artificially using one or more chemical or biological reagents that increases affinity of the intact cell to the surface.

6. The method according to claim 1, wherein in step (b), the RT primer further comprises a well-specific barcode sequence (WID), and wherein the method further comprises concentrating the released cDNA as a step (d2), after step (d) and before step (e).

7. The method according to claim 1, wherein the method further comprises concentrating cDNA containing the 5' PCR handle 1 and the 3' PCR handle 2 as a step (e2), after step (e).

8. The method according to claim 1, wherein the method further comprises the step:

(f) a first amplifying of the cDNA containing the 5' PCR handle 1 and the 3' PCR handle 2 from step (e) in order to obtain a first product mix.

9. The method according to claim 8, wherein the method further comprises the steps of:

(g) a PCR extension step using indexing primers comprising a PCR handle 3 or a PCR handle 4, complementary to the 5' PCR handle 1 and 3' PCR handle 2, respectively, in order to obtain a second product mix, and (h) a second PCR amplifying of the second product mix obtained in step (g) using PCR primers complementary to the PCR handles 3 and 4 in order to obtain a third product mix.

10. The method according to claim 9, wherein in step (g) indexing primers are used comprising plate indicating sequences (PIDS), said PIDS being a first PIDS on the 3' primer and a second PIDS on the 5' primer.

11. The method according to claim 9, wherein in step (g) the PCR extension step is performed with a PIDS on either of the 3' or 5' primer and/or well-specific barcode sequence (WID) on either of the 3' or 5' primer.

12. The method according to claim 11, wherein the separate volumes of the third product mix are pooled prior to a sequencing.

13. The method according to claim 1, wherein in step (b) the RT primers further comprise either a plate indicating sequences (PIDS) or well-specific barcode sequence (WID) and a PCR handle 3, and the adapter molecule in step (e) further comprises either a PIDS or a WID and a PCR handle 4, under the provision that the RT primers and the adapter molecule do not contain the same identification sequence.

14. The method according to claim 1, further comprising an imaging step of the intact cells after step (d).

15. A method of forming complementary DNA (cDNA) sequencing libraries from RNA in situ comprising steps of:

(a) fixating intact cell-like particles, immobilized on a solid surface, (b) performing an in situ reverse transcription (RT) inside the intact cell-like particles, using RT primers comprising a 5' PCR handle 1, and deoxynucleotide triphosphates (dNTPs), wherein the dNTPs include biotinylated dNTPs;

(c) releasing single stranded cDNA from the intact cell-like particles using a release mix, wherein the release mix comprises an RNAse, such that the single stranded cDNA is released from intact cell-like particles without lysing the intact cell-like particles;

(d) collecting a supernatant comprising released cDNA into a single larger volume or in separate volumes; and (e) introducing, by ligation or polymerase extension, an adapter molecule comprising a 3' PCR handle 2 that will bind 3' of the cDNA.

16. The method according to claim 15, wherein the intact cell-like particles are viral particles.

17. The method according to claim 3, wherein the intact cells comprise epithelial primary cells.

18. The method according to claim 3, wherein the intact cells comprise bacteria from Genera *Bacteroides, Clostridium, Faecalibacterium, Eubacterium, Ruminococcus, Peptococcus, Peptostreptococcus, Bifidobacterium, Escherichia,* or *Lactobacillus.*

* * * * *